United States Patent [19]
Askin et al.

[11] Patent Number: 5,612,484
[45] Date of Patent: Mar. 18, 1997

[54] PROCESS FOR MAKING HIV PROTEASE INHIBITORS

[75] Inventors: David Askin; Jess Sager, both of Warren; Kai Rossen, Westfield; Ralph P. Volante, Cranbury; Paul J. Reider, Westfield, all of N.J.

[73] Assignee: Merck & Co., Inc., Rahway, N.J.

[21] Appl. No.: 443,631

[22] Filed: May 18, 1995

[51] Int. Cl.[6] .................................................. C07D 401/06
[52] U.S. Cl. ........................... 544/360; 544/388; 544/390
[58] Field of Search ................................... 544/388, 390, 544/360

[56] References Cited

FOREIGN PATENT DOCUMENTS 541168   5/1993   European Pat. Off. .

OTHER PUBLICATIONS

Giraud–Clenet, et al., Compt. Rend., t. 262, pp. 224–227, 1966.
Krimen, et al., "The Ritter Reaction", Organic Reactions, vol. 17, pp. 213–325, 1969.
Mowry, et al., "The Preparation of Nitriles", Chem. Rev., 42, pp. 189–283, 1947.
Ugi, et al., "The Passerini and Ugi Reactions", Comprehensive Organic Synthesis, vol. 4, pp. 1083–1109, 1991.

*Primary Examiner*—Joseph McKane
*Assistant Examiner*—Richard S. Myers, Jr.
*Attorney, Agent, or Firm*—Mary A. Appollina; Melvin Winokur

[57] ABSTRACT

A process for making a clinically efficacious HIV protease inhibitor Compound J eliminates one step in its synthesis, by an improved, alternative synthesis of the 2(S)-4-picolyl-2-piperazine-t-butyl-carboxamide intermediate.

1 Claim, No Drawings

5,612,484

PROCESS FOR MAKING HIV PROTEASE INHIBITORS

FIELD OF THE INVENTION

The present invention is concerned with novel intermediates and processes for synthesizing compounds which inhibit the protease encoded by human immunodeficiency virus (HIV), and in particular, the compound disclosed and referred to as "Compound J" in EPO 541,168, which published on May 12, 1993, or pharmaceutically acceptable salts thereof.

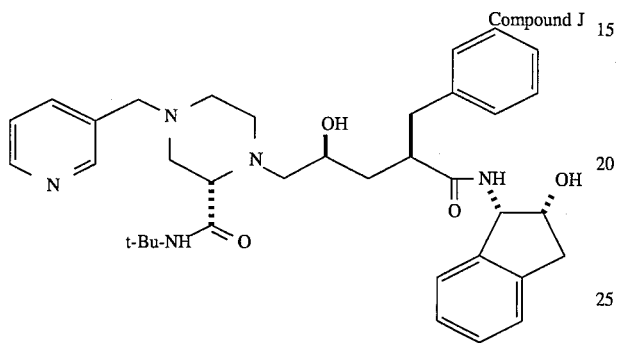

Compound J

Compound J and analogs are of value in the prevention of infection by HIV, the treatment of infection by HIV and the treatment of the resulting acquired immune deficiency syndrome (AIDS). These compounds are also useful for inhibiting renin and other proteases. More specifically, the instant invention provides novel processes for synthesizing piperazine-ten-butyl-carboxamide derivatives which are key intermediates useful in the preparation of HIV protease inhibitor compounds, including Compound J.

BACKGROUND OF THE INVENTION

A retrovirus designated human immunodeficiency virus (HIV) is the etiological agent of the complex disease that includes progressive destruction of the immune system (acquired immune deficiency syndrome; AIDS) and degeneration of the central and peripheral nervous system. This virus was previously known as LAV, HTLV-III, or ARV. A common feature of retrovirus replication is the extensive post-translational processing of precursor polyproteins by a virally encoded protease to generate mature viral proteins required for virus assembly and function. Inhibition of this processing prevents the production of normally infectious virus. For example, Kohl, N. E. et al., *Proc. Nat'l Acad. Sci.*, 85, 4686 (1988), demonstrated that genetic inactivation of the HIV encoded protease resulted in the production of immature, non-infectious virus particles. These results indicate that inhibition of the HIV protease represents a viable method for the treatment of AIDS and the prevention or treatment of infection by HIV.

The nucleotide sequence of HIV shows the presence of a pol gene in one open reading frame [Ratner, L. et al., *Nature*, 313,277 (1985)]. Amino acid sequence homology provides evidence that the pol sequence encodes reverse transcriptase, an endonuclease and an HIV protease [Toh, H. et al., *EMBO J.*, 4, 1267 (1985); Power, M. D. et al., *Science*, 231, 1567 (1986); Pearl, L. H. et al., *Nature*, 329, 351 (1987)]. The end product compounds, including Compound J which is shown in Example 29 below, that can be made from the novel intermediates and processes of this invention are inhibitors of HIV protease, and are disclosed in EPO 541,168, which published on May 12, 1993.

Previously, the synthesis of Compound J and related compounds was accomplished via a 12-step procedure. This procedure is illustrated in EPO 541,168. In prior methods, the HIV protease inhibitor J was prepared by coupling of the epoxide intermediate 2 with the Boc-protected piperazine carboxamide 4 to afford the Boc-protected coupled intermediate 5. Deblocking of 5 then afforded a penultimate Compound 6 which was subjected to picolylation to afford J. The disadvantage with this route is that three chemical steps are necessary to convert the epoxide 2 to J. Thus, after deblocking, a separate picolylation step is necessary to effect conversion to J.

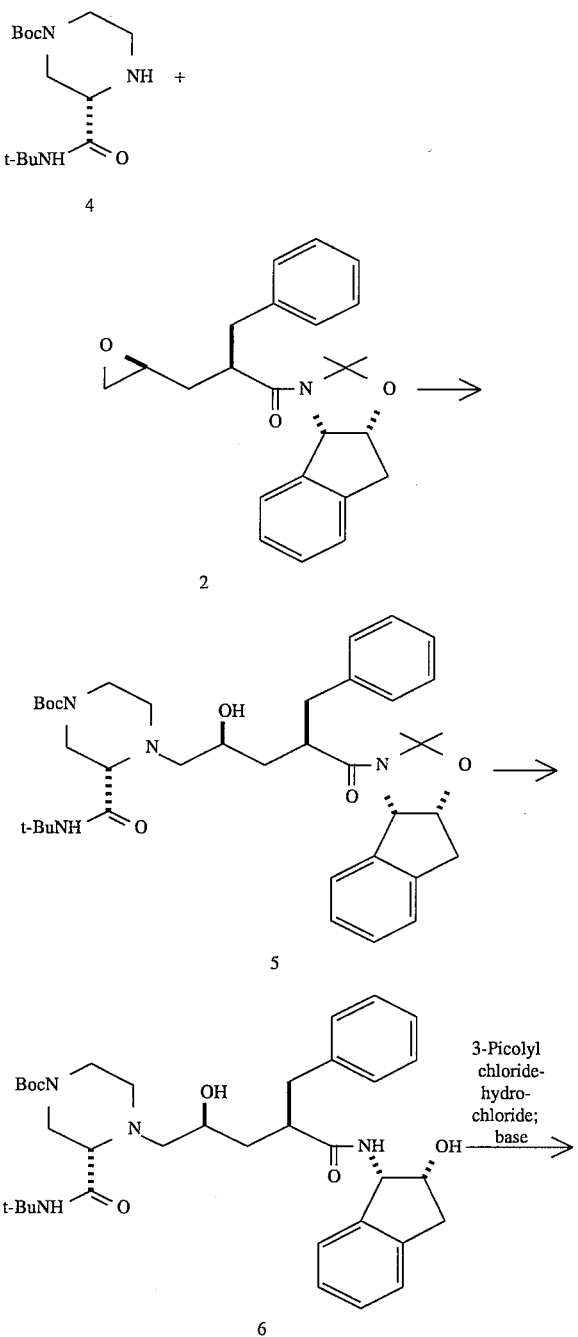

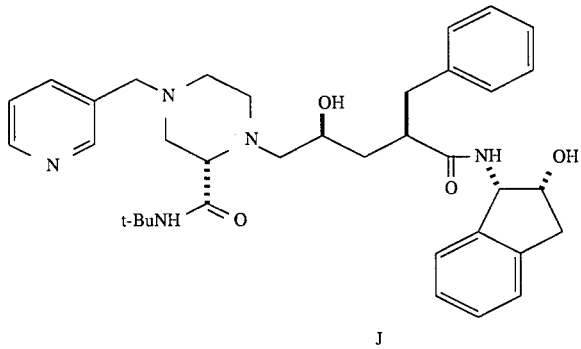

J

Since the more reactive 4-position of the piperazine carboxamide must be protected prior to coupling, the most efficient blocking method for the chiral 2-piperazine-t-bu- tylcarboxamide would be the incorporation of the 3-picolyl moiety at this point, i.e., piperazine 1. However, it was unexpected that the reaction of piperazine 1 with epoxide 2 would be efficient, since piperazine 1 contains three basic amine functions capable of attacking the epoxide 2. The Boc-protected piperazine 4, however, contains only one basic amine function, and thus it was expected that the coupling of 2 and 4 would be straightforward.

More recently, a convenient process to prepare the HIV protease inhibitor J from the 4-picolyl piperazine carboxamide 1 via a two-step procedure has been discovered. The piperazine 1 is condensed with epoxide 2 to afford the coupled product 3. Removal of the acetonide protecting group of 3 directly affords the HIV-1 protease inhibitor J.

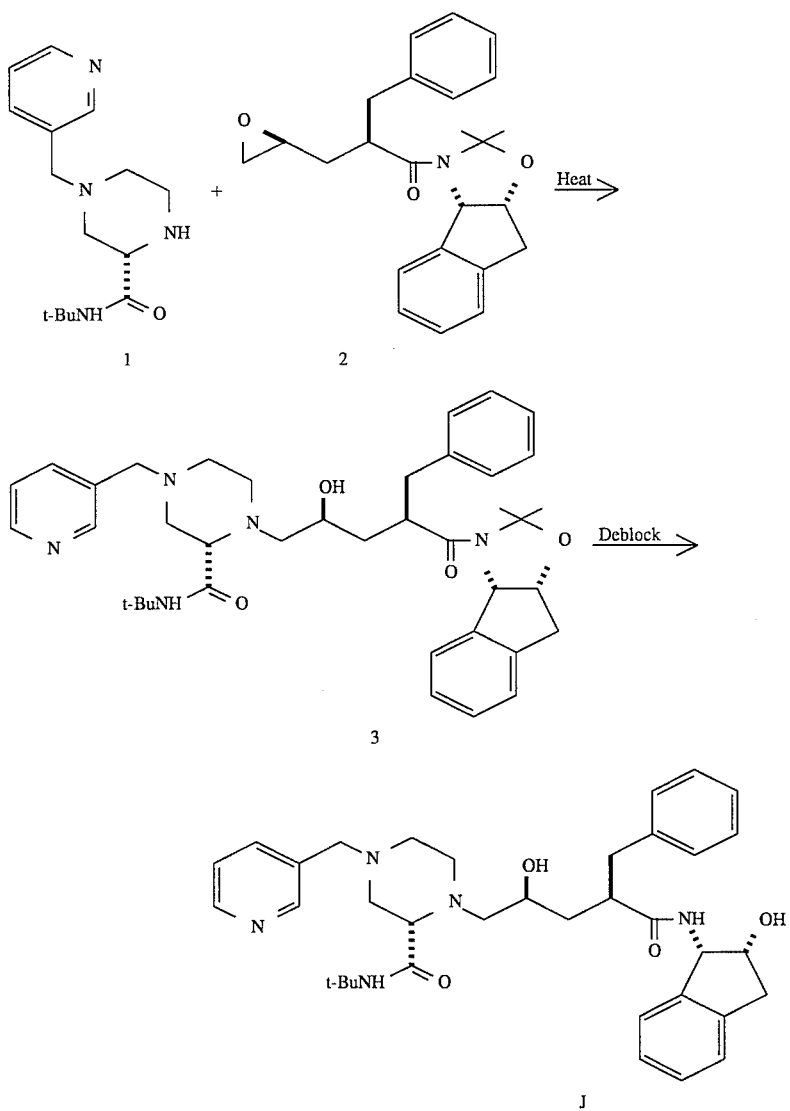

The synthesis of the chiral piperazine-2-carboxamide intermediates is currently achieved in a stepwise manner from an aromatic 2-pyrazine carboxylic acid precursor. First, the t-butylcarboxamide is prepared from commercially available pyrazine-2-carboxylic acid by activation as the acid chloride followed by reaction with t-butylamine to form pyrazine-2-t-butylcarboxamide. Subsequently, the pyrazine ring is reduced through a hydrogenation to afford racemic piperazine t-butylcarboxamide. If resolution is required, it can be effected at this point via optically active acids to obtain optically enriched material. In the case of the Compound J intermediate, the resolution is carried out at this stage with either (S)-10-camphorsulfonic acid or L-pyroglutamic acid to afford the desired (S)-antipode. A protection to differentiate $N_1$ and $N_4$ of the piperazine then affords predominantly the desired 4-protected piperazine derivative. In the case of the Compound J intermediate, the protection is carded out with di-t-butyldicarbonate and affords about a 9:1 ratio of $N_4$-BOC protected product and 1,4-bis-protected product. If the reaction is carded out with 3-picolyl chloride to introduce the 3-picolyl group at the 4-piperazine position in Compound J, however, very low selectivities result (4:1 mono/bis alkylation), which affords a mixture that cannot be purified by crystallization. This method for preparing the piperazine-2-t-butylcarboxamide intermediates require several distinct steps and is labor intensive and complicated from a factory design standpoint. Thus, a need remains for a more efficient and simplified process for making the key piperazine-2-carboxamide intermediates.

*Rev.*, 42; 236, (1948)] are well-known methods for the preparation of amino acids and peptide derivatives. The characteristic feature of the Ugi reaction is the α-addition of an isocyanide and the anion X of a suitable acid HX to an iminium ion (40), followed by a spontaneous rearrangement of the α-adduct (41) into a stable α-aminocarboxamide derivative (42).

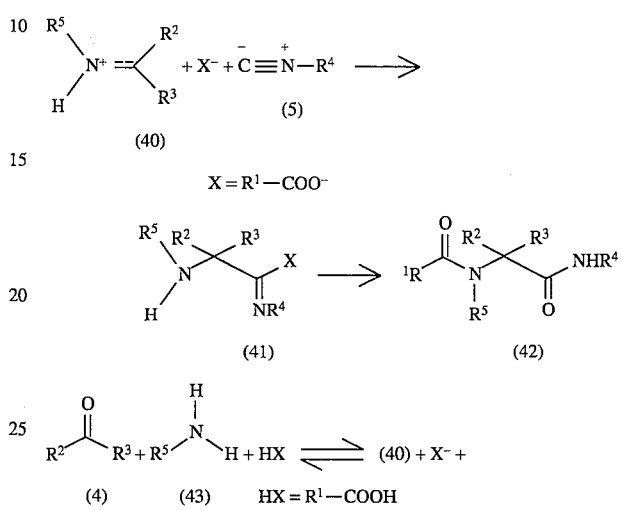

The four component Ugi condensation [Ivar Ugi, et al., in *Comprehensive Organic Synthesis*, Vol. 2, page 1083 (B. M. Trost, ed. and Strecker condensation [D. T. Mowry, *Chem.*

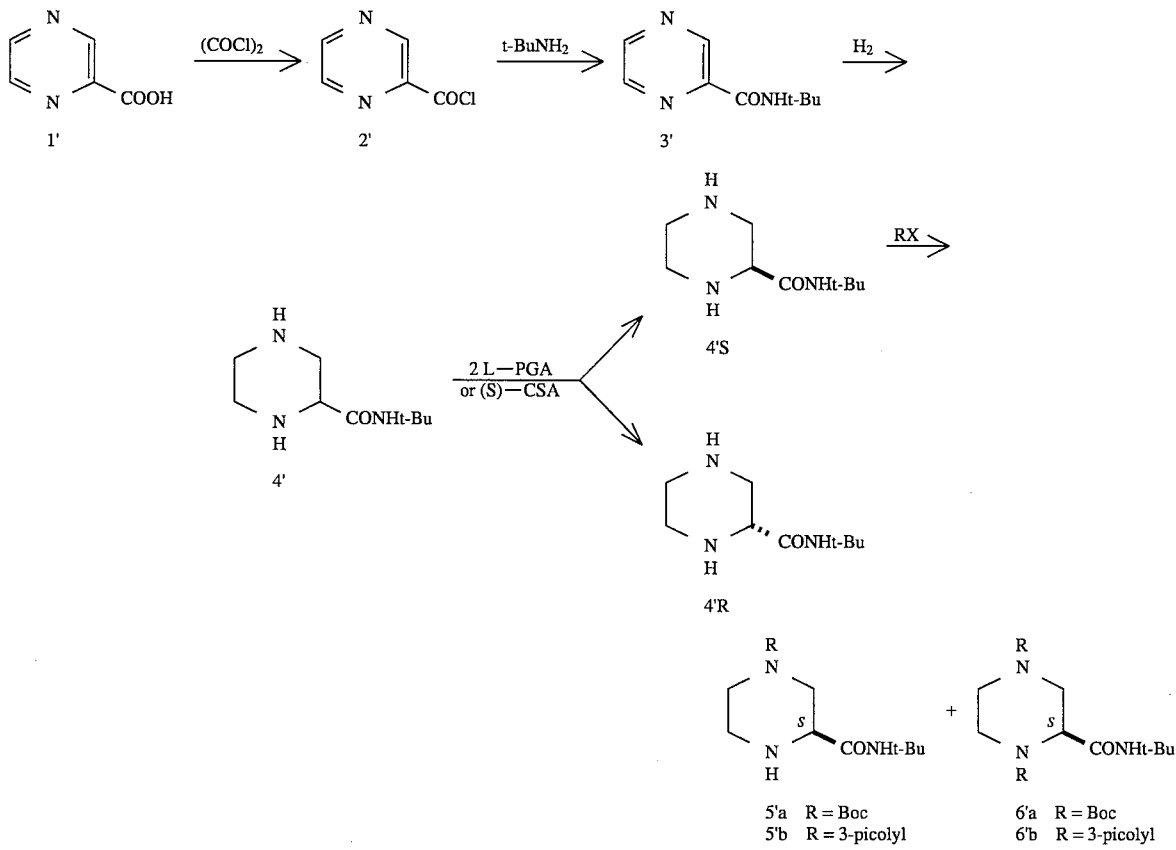

-continued

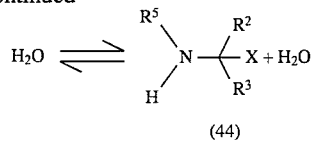
(44)

Thus, the product results from four distinct reactants, namely (4), (5), (43) and HX, through a condensation reaction. Therefore, such an Ugi reaction was initially called the four-component condensation (4CC). While in principle a very powerful method, the Ugi reaction was unknown for the preparation of piperazine carboxamides.

The Strecker synthesis of amino acids has proven extremely useful to synthetic organic chemists since its discovery in 1850. Strecker treated acetaldehyde ammonia with hydrogen cyanide and hydrolyzed the product to obtain alanine. [D. T. Mowry, *Chem. Rev.*, 42, 236 (1948)]

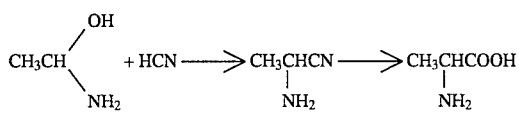

In its most general form, the Ritter reaction [L. I. Krimen and D. J. Cota, *Organic Reactions*, Vol. 17, 213 (1969)] involved the nucleophilic addition of a nitrile to a carbonium ion in the presence of sulfuric acid.

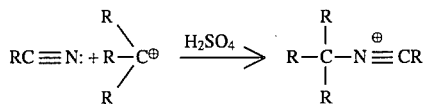

Subsequent dilution with water yields the amide.

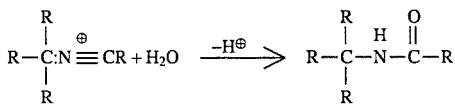

While the Strecker synthesis is known to afford 2-amino acids after hydrolysis of the corresponding 2-aminonitriles, the analogous Ritter reaction of the aminonitriles to directly afford the 2-aminocarboxamide derivatives is not well known. Moreover, this transformation is unexpected since 2-aminonitriles have been reported to undergo undesired conversions to the 2-hydroxy-carboxamide products in the Ritter reaction [D. Giraud-Clenet and J. Anatol, *Compt. Rend.*, 262, 244 (1966)].

It has now been found that the Ugi reaction, as well as the Strecker and Ritter reactions, can be employed in the synthesis of the piperazine 2-carboxamide intermediates. Thus, the present invention provides improved methods for forming the key intermediates with increased simplicity and efficiency, resulting in savings in capital and labor. Additionally, the improved methods of the present invention result in decreased formation of waste by-products than in previously known methods for forming the key piperazine-2-carboxamide intermediates.

SUMMARY OF THE INVENTION

The present invention provides processes for making compounds of formula (III)

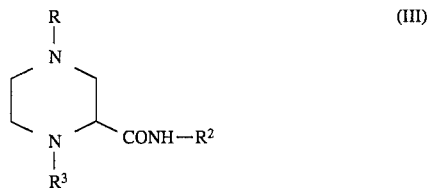
(III)

which are key intermediates in the formation of HIV protease inhibitors, including Compound J. In the compounds of formula (III), R is selected from hydrogen, $C_{1-10}$ alkoxycarbonyl or unsubstituted or substituted $C_{1-10}$ alkyl wherein said substituent is aryl or heteroaryl; $R^2$ is $C_{1-10}$ alkyl or aryl; and $R^3$ is hydrogen or $-COR^1$ wherein $R^1$ is selected from hydrogen, $C^{1-10}$ alkyl, mono-, di- or tri-halogenated $C_{1-10}$ alkyl or aryl. Preferably, $R^2$ is t-butyl.

In one embodiment of the present invention is a process for forming a compound (F)

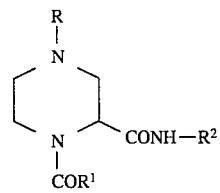
F wherein R, $R^1$ and $R^2$ are as defined above; comprising reacting an imine (C)

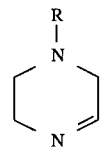
C with an isocyanide compound $R^2NC$ in the presence of a carboxylic acid, $R^1-CO_2H$, to form the compound (F)

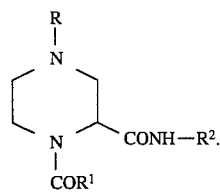
F

In a class of this embodiment is the process, further comprising the step of deblocking the compound (F) to form a compound (I)

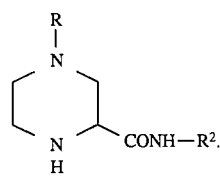
I

In a subclass is the process wherein the imine (C)

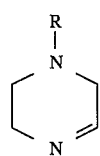 C is formed by reacting an ethylene diamine compound A of the formula $H_2N(CH_2)_2NHR$ with a halogenated acetaldehyde or a halogenated acetaldehyde di-$C_{1-2}$ alkylacetal.

Illustrative of this embodiment is the process wherein the compound (F)

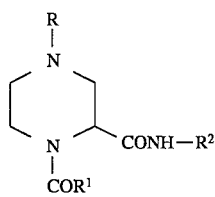 F is prepared in one-pot without first isolating the imine (C)

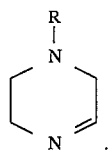 C

In a second embodiment of the present invention is a process for forming an amide (G)

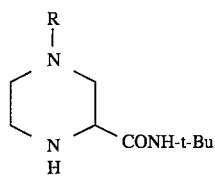 G wherein R is as defined above; comprising reacting a nitrile (H)

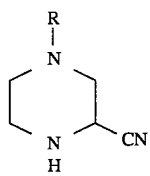 H with a compound selected from t-butanol, isobutylene or t-butyl ester in the presence of a strong acid to form the amide (G)

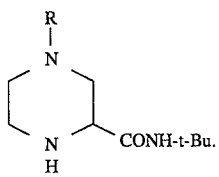 G

In a class of this second embodiment is the process wherein the strong acid is selected from $H_2SO_4$, $H_3PO_4$, $CH_3SO_3H$ or $BF_3$. Preferably, the strong acid is $H_2SO_4$.

In a subclass of this second embodiment is the process wherein the nitrile (H)

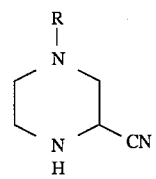 H is prepared by reacting an imine (C)

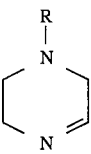 (C)

with a cyanide ion to form the nitrile (H).

Illustrative of this second embodiment is the process wherein the imine (C)

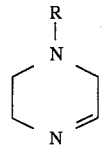 C is formed by reacting an ethylene diamine compound A of the formula $H_2N(CH_2)_2NHR$ with a halogenated acetaldehyde or a halogenated acetaldehyde di-$C_{1-2}$ alkylacetal.

An illustration of this second embodiment is the process wherein preparation of nitrile (H)

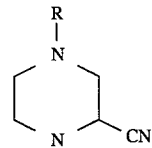 H is accomplished in one-pot without first isolating the imine (C)

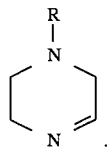 (C)

Exemplifying the present invention is any of the processes described above wherein R is substituted $C_{1-5}$ alkyl where said substituent is heteroaryl. Preferably, R is 3-picolyl.

An example of the present invention is any of the processes described above, further comprising the step of resolving the racemic compound

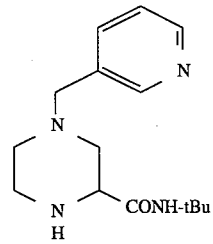

to isolate a compound 1

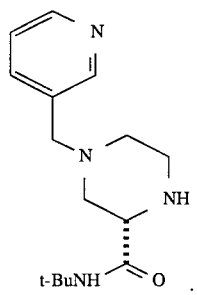

Further illustrating the invention is any of the processes described above, further comprising the step of reacting the compound 1

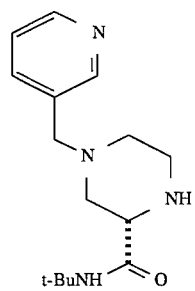

with a compound 2

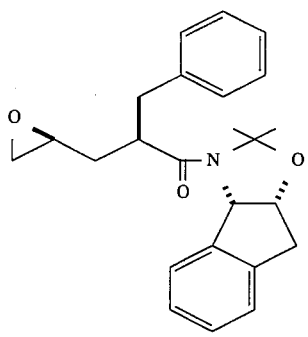

to form a compound 3

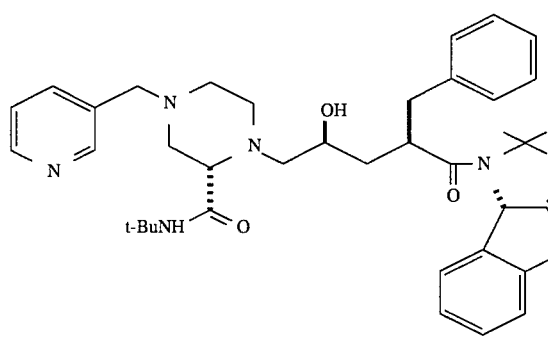

Another illustration of the present invention is any of the processes described above, further comprising the step of deblocking the compound 3 to form a compound J

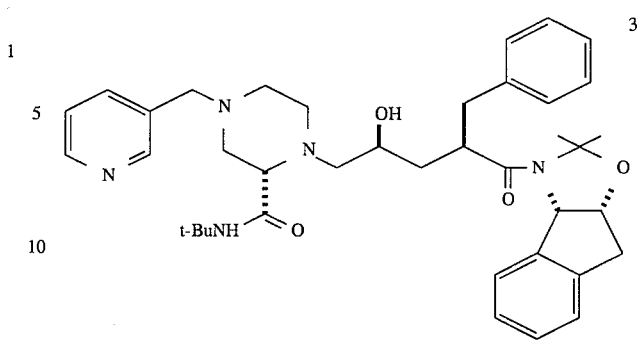

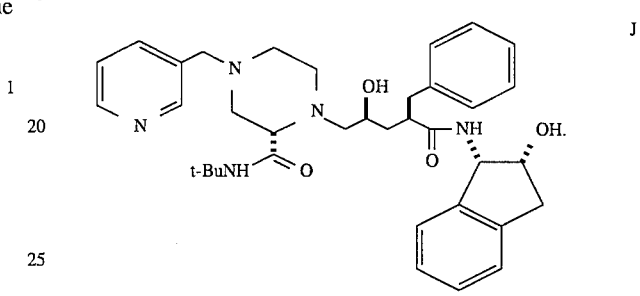

Further exemplifying the present invention is a compound selected from

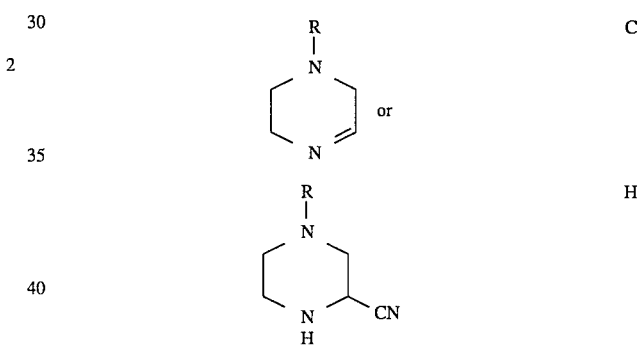

wherein R is selected from hydrogen, $C_{1-10}$ alkoxycarbonyl or unsubstituted or substituted $C_{1-10}$ alkyl where said substituent is aryl or heteroaryl. Preferably, R is substituted $C_{1-5}$ alkyl where said substituent is heteroaryl. Most preferably, R is 3-picolyl.

More particularly illustrating the invention is a process for forming a compound (I)

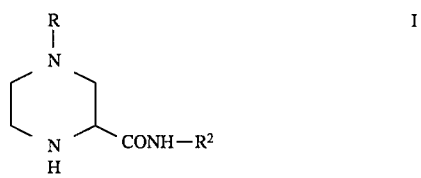

wherein R is selected from hydrogen, $C_{1-10}$ alkoxycarbonyl or unsubstituted or substituted $C_{1-10}$ alkyl wherein said substituent is aryl or heteroaryl; and $R^2$ is $C_{1-10}$ alkyl or aryl; comprising (a) reacting (A), (B), (E) and (D) to form a compound (F)

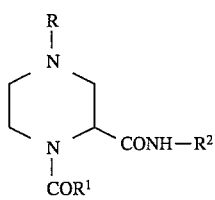

wherein (A) is $H_2N-(CH_2)_2-NHR$ where R is as defined above; (B) is selected from a halogenated acetaldehyde or a halogenated acetaldehyde $C_{1-2}$ alkylacetal; (E) is $R^1CO_2H$ where $R^1$ is selected from hydrogen, $C_{1-10}$ alkyl, mono-, di- or tri-halogenated $C_{1-10}$ alkyl or aryl; and (D) is $R^2NC$ where $R^2$ is as defined above; and (b) deblocking the compound (F)

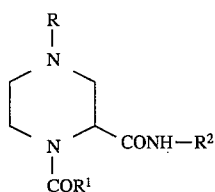

to form the compound (I)

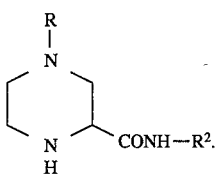

More specifically exemplifying the invention is a process for forming an amide (G)

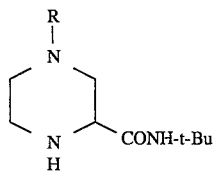

wherein R is selected from hydrogen, $C_{1-10}$ alkoxycarbonyl or unsubstituted or substituted $C_{1-10}$ alkyl wherein said substituent is aryl or heteroaryl; comprising (a) reacting a compound (A), $H_2N-(CH_2)_2-NHR$ where R is as defined above, a compound (B) selected from a halogenated acetaldehyde or a halogenated acetaldehyde $C_{1-2}$ alkylacetal and a cyanide ion to form a nitrile (H)

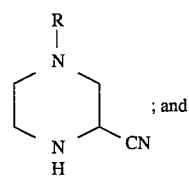

; and (b) reacting the nitrile (H) with a compound selected from t-butanol, isobutylene or t-butyl ester in the presence of a strong acid to form the amide (G)

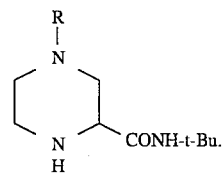

DETAILED DESCRIPTION OF THE INVENTION

During the synthesis of compounds which inhibit HIV protease, and in particular Compound J, a key intermediate is the piperazine-2-tert-butylcarboxamide derivative G

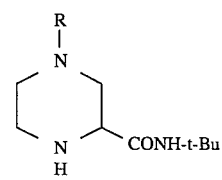

or salts thereof. To prepare the key intermediate G, ethylene diamine or a mono-alkylated derivative thereof (A) is condensed with chloro-acetaldehyde (B) to give an intermediate imine (C). Bromoacetalde-hyde, chloroacetaldehyde dimethylacetal or bromoacetaldehyde diethylacetal can be used in place of chloroacetaldehyde to form the imine. The reaction for preparing the imine (C) can be carried out in the presence of a suitable solvent at temperatures between –20° C. and 150° C., preferably, between –20° C. and 80° C., most preferably, between 0° C. and 70° C. Suitable solvents include esters, aromatic hydrocarbons, halogenated solvents, alcohols and water. Preferably, the solvent is selected from water or alcohols; most preferably, methanol, ethanol, propanol, or mixtures thereof. In the Ugi based variant of the present invention, the piperazine ting and the amide bond are formed in one pot from the imine (C) by condensation of t-butyl isocyanide (D) and a carboxylic acid (E) to afford the 1-acyl-piperazine-2-t-butylcarboxamide derivative (F). If desired, carboxamides other than t-butyl can be prepared by utilizing different $C_{1-10}$ alkyl isocyanides or aryl isocyanides in place of t-butylisonitrile (D). Carboxylic acids which can be employed in the instant process include, but are not limited to, formic acid, acetic acid, benzoic acid, trifluoroacetic acid, chloroacetic acid, dichloroacetic acid or trichloroacetic acid. Alternatively, the carboxylic acid can be generated in situ from a salt of the acid and the HCl or HBr generated in the alkylation. Solvents suitable for use in the Ugi reaction are the same as those described above for preparation of the imine (C). The Ugi reaction can be carried out at temperatures between –20° C. and 150° C., preferably, between 0° C. and 80° C. Deblocking of the 1-acyl group then affords the 2-piperazine-t-butyl carboxamide derivative (G) as shown in Scheme I. Methods for removing the 1-acyl group are readily known to those of ordinary skill in the art See e.g., Greene, T. W.; Wuts, P. G. M., Protective Groups in Organic Synthesis (2d ed. 1991).

SCHEME I

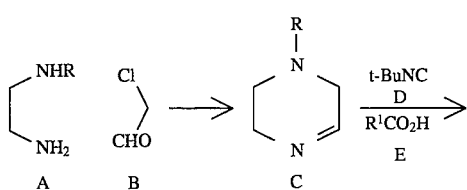

15
-continued
SCHEME I

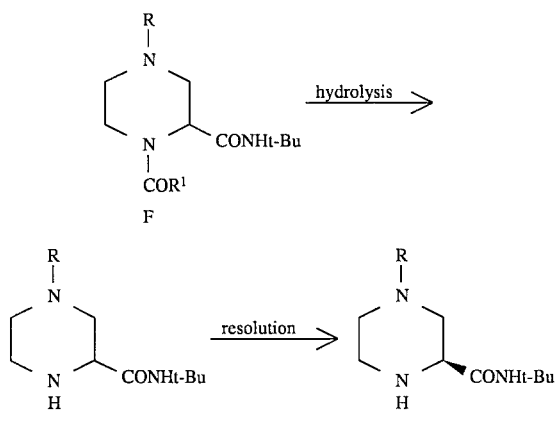

In an alterative embodiment of the present invention, the intermediate imine (C) is reacted with cyanide ion (e.g., NaCN, KCN, LiCN, HCN) in the Strecker variant of the instant process to afford the aminonitrile (H). The reaction for preparing the aminonitrile (H) can be carded out in the presence of a suitable solvent at temperatures between −20° C. and 150° C., preferably, between −20° C. and 80° C., most preferably, between 0° C. and 70° C. Suitable solvents include esters, aromatic hydrocarbons, halogenated solvents, alcohols and water. Preferably, the solvent is selected from water or alcohols; most preferably, methanol, ethanol, propanol, or mixtures thereof, are utilized. The aminonitrile (H), in turn, is readily convened to the piperazine-2-t-butylcarboxamide derivative (G) via an acid catalysed Ritter reaction with t-butanol as shown in Scheme II. More specifically, the Ritter reaction is conducted by reacting the aminonitrile (H) with isobutylene, t-butanol or a t-butyl ester in combination with a strong acid such as $H_2SO_4$, $H_3PO4$, $CH_3SO_3H$ or $BF_3$. Preferably, sulfuric acid is used. The Ritter reaction for preparation of (G) from the aminonitrile (H) can be carried out at temperatures between −20° C. and 150° C., preferably, between 0° C. and 50° C., neat or in the presence of a solvent such as an alkane, an aromatic solvent, a halogenated solvent or an ester. Preferred solvents are the excess reagents (i.e., neat) or halogenated solvents such as methylene chloride or chloroform.

SCHEME II

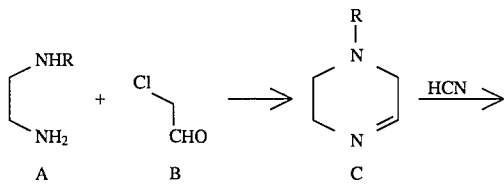

16
-continued
SCHEME II

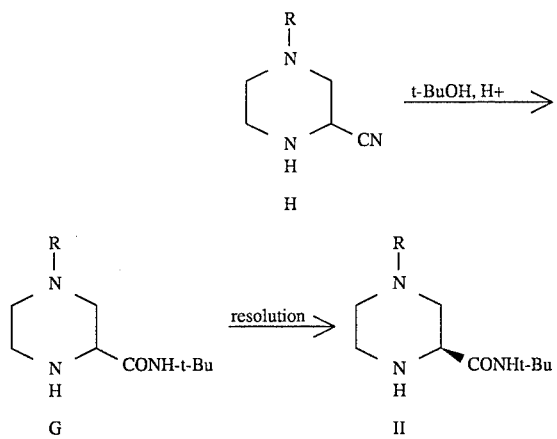

In the one pot variation of this reaction which leads directly to the formation of (F) in the Ugi reaction or (H) in the Strecker reaction, it is not necessary to postulate the imine (C) as an intermediate. It is also possible that first the Ugi or Strecker reaction takes place, followed by N-alkylation and ring closure to form the piperazine (F) or (H).

Once the piperazine-2-carboxamide derivative (G) is formed, separation of the (S) and (R) enantiomers is necessary in order that the desired (S)-antipode II may be carried on to form the HIV protease inhibitor compounds described in EPO 541,168, and in particular, Compound J. Separation of the enantiomers can be effected according to methods well known to those skilled in the art, for example, chiral HPLC. Alternatively, separation of the (S) and (R) enantiomers can be effected by preparing the (S)-camphorsulfonic acid or (L)-pyroglutamic acid salts of the piperazine-2-carboxamide derivative from racemic compound.

The coupling can be carried out by heating compound H (e.g., piperazine 1) and the epoxide 2 neat or in a variety of solvents. The coupling reaction can be carried out at temperatures ranging from 25° C. to 150° C., preferred is the range of 50° C. to 120° C. with the most preferred temperatures being 65° C. to 85° C. Desired solvents for this step include esters such as ethyl acetate, isopropyl acetate, n-butyl acetate; acetonitrile; alcohols such as methanol, ethanol, n-propanol, n-butanol, t-butanol, t-amyl alcohol and isopropanol; hydrocarbons such as cyclohexane and toluene; ethers such as THF and DME; and formamides such as DMF. Preferred solvents are alcohols with the most preferred being methanol and isopropanol.

The deblocking of intermediate 3 to J is accomplished by standard methods, i.e., treatment with strong acids such as gaseous HCl in alcoholic solvents or aqueous HCl with gaseous HCl being the most preferred method.

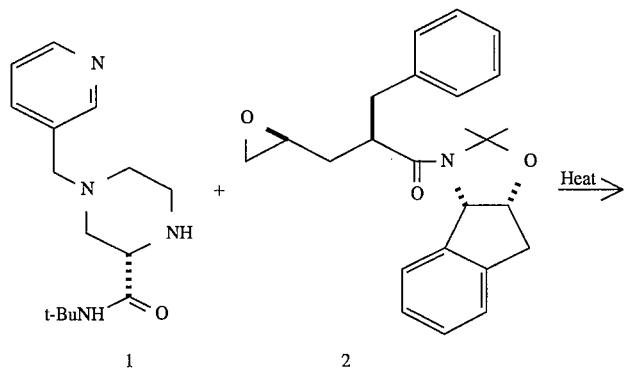
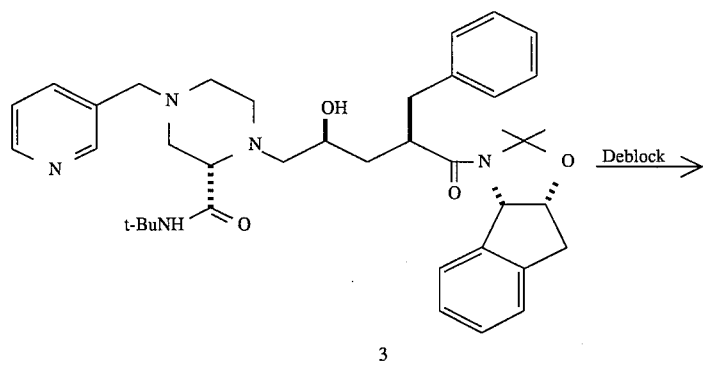
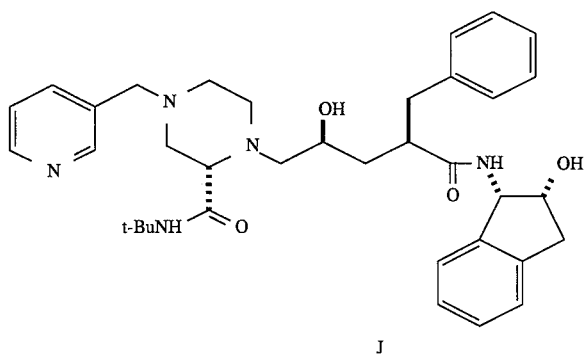
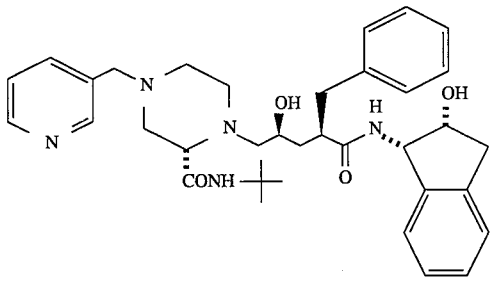

The processes and intermediates of this invention are useful for the preparation of end-product compounds that are useful in the inhibition of HIV protease, the prevention or treatment of infection by the human immunodeficiency virus (HIV), and the treatment of consequent pathological conditions such as AIDS. These end-product compounds and their ability to inhibit HIV protease are described in EPO 541,168, which published on May 12, 1993. Treating AIDS or preventing or treating infection by HIV is defined as including, but not limited to, treating a wide range of states of HIV infection: AIDS, ARC (AIDS related complex), both symptomatic and asymptomatic, and actual or potential exposure to HIV. For example, the end-product compounds that can be made from the processes and intermediates of this invention are useful in treating infection by HIV after suspected past exposure to HIV by, e.g., blood transfusion, organ transplant, exchange of body fluids, bites, accidental needle stick, or exposure to patient blood during surgery.

The end-product HIV protease inhibitors are also useful in the preparation and execution of screening assays for antiviral compounds. For example, end-product compounds are useful for isolating enzyme mutants, which are excellent screening tools for more powerful antiviral compounds. Furthermore, such compounds are useful in establishing or determining the binding site of other antivirals to HIV protease, e.g., by competitive inhibition. Thus, the end-product compounds that are made from the processes and intermediates of this invention are commercial products to be sold for these purposes.

The end product HIV protease inhibitor compound J has the structure or pharmaceutically acceptable salts or hydrates thereof. Compound J is named N-(2(R)-hydroxy-1(S)-indanyl)-2(R)-phenylmethyl-4(S)-hydroxy-5-(1(4-(3-pyridylmethyl)-2(S)-N'-(t-butylcarboxamido)-piperazinyl))-pentaneamide;

[1S-[1α[αS*,γR*,δ(R*)],2α]]-N-(2,3-dihydro-2-hydroxy-1H-inden-1-yl)-2-[[(1,1-dimethylethyl)amino]carbonyl]-γ-hydroxy-α-(phenyl-methyl)-4-(3-pyridinylmethyl)-2-piperazinepentaneamide; or N-(1(S)-2,3-dihydro-2(R)-hydroxy-1H-indenyl)-4(S)-hydroxy-2(R)-phenylmethyl-5-[4-(3-pyridylmethyl)-2(S)-t-butylcarbamoyl)piperazinyl]pentaneamide.

HIV protease inhibitor compounds that can be made from the processes of the instant invention are disclosed in EPO 541,164. The HIV protease inhibitory compounds may be administered to patients in need of such treatment in pharmaceutical compositions comprising a pharmaceutical carder and therapeutically-effective amounts of the compound or a pharmaceutically acceptable salt thereof. EPO 541,164 discloses suitable pharmaceutical formulations, administration routes, salt forms and dosages for the compounds.

The compounds of the present invention, may have asymmetric centers and occur as racemates, racemic mixtures and as individual diastereomers, or enantiomers with all isomeric forms being included in the present invention. Also included within the scope of the invention are polymorphs and hydrates of the compounds of the instant invention.

When any variable (e.g., aryl) occurs more than one time in any constituent, its definition on each occurrence is independent of its definition at every other occurrence. Also, combinations of substituents and/or variables are permissible only if such combinations result in stable compounds.

The term "halogen," as used, herein includes fluorine, chlorine, bromine and iodine, especially chlorine and bromine.

As used herein except where noted, "alkyl" is intended to include both branched- and straight-chain saturated aliphatic hydrocarbon groups having the specified number of carbon atoms (Me is methyl, Et is ethyl, Pr is propyl, Bu is butyl; t-Bu is tert-butyl). As used herein, "aryl" is intended to mean phenyl (Ph) or naphthyl. "Heteroaryl," as used herein, is intended to mean a 6-membered aromatic heterocyclic ring or a stable 8- to 10-membered unsaturated bicyclic heterocycle wherein the mono- or bicyclic- heterocyle consists of carbon atoms and one to three heteroatoms selected from the group consisting of N, O or S. For example, the term "heteroaryl" would include, but is not limited to, the following moieties.

Abbreviations used in the instant specification, particularly the Schemes and Examples, are as follows:

Boc or BOC=t-butyloxycarbonyl
CSA=camphorsulfonic acid
EtOAc=ethyl acetate
GC=gas chromatography
HPLC=high pressure liquid chromatography
HOAc=acetic acid
iPrOAc or IPAC or IPAc=isopropyl acetate
i-PrOH=isopropanol
LC=liquid chromatography
LDS=lithium hexamethyldisilazide
MeOH=methanol
NCS=N-chlorosuccinimide
NaOMe=sodium methoxide
n-PrOH=n-propanol
NMR=nuclear magnetic resonance
THF=tetrahydrofuran
TLC=thin layer chromatography Representative experimental procedures utilizing the novel process are detailed below. These procedures are exemplary only and are not limitations on the novel process of this invention. Unless indicated otherwise, all $^1$H NMRs were run on a 250 MHz instrument and all $^{13}$C NMRs were run on a 62 MHz instrument.

EXAMPLE 1

1-Phenylcarboxy-4-(3-picolyl)-2-tert-butylcarboxamide-piperazine

| | |
|---|---|
| 3-Picolyl ethylenediamine | 1.395 g (9.23 mmol) |
| Chloroacetaldehyde 50 wt % in H$_2$O | 1.14 mL (9.23 mmol) |
| NaHCO3 | 0.78 g (9.23 mmol) |
| Benzoic acid | 1.13 g (9.23 g) |
| tert-Butyl isocyanide | 1.25 mL (21.0 mmol) |
| MeOH | 9.5 mL |

To a solution of 3-picolyl ethylenediamine and benzoic acid in MeOH was added the NaHCO₃ and the chloroactaldehyde solution. It was heated to 40° C. over 15 min and the tert-butyl isocyanide was added. The reaction was stirred at 40° C. for 38 h and 15 mL of 5N NaOH were added to the reaction mixture. The reaction mixture was extracted with CH₂Cl₂ (150 mL) and the organic phase was washed with 10 mL of water. The organic phase was concentrated to dryness and the resulting oil was purified by chromatography on SiO₂ (EtOAc 100% to EtOAc/MeOH 85/15). Concentration of the product containing fractions gave 1-phenylcarboxy-4-(3-picolyl)-2-tert-butylcarboxamide-piperazine as a tan solid. mp 134° C.; ¹H NMR (CDCl₃, CF₃COOD) 9.5 (s, 1H), 9.1 (d, 1H), 8.9 (d, 1H), 8.2 (dd, 1H), 7.6 (m, 5H), 5.6 (b, 1H 4.9 (dd, 2H), 4.3 (m, 1H), 4.2 (d, 1H), 3.7 (m, 4H), 1.4 (s, 9H).

EXAMPLE 2

1-Carboxy-4-(3-picolyl)-2-tert-butylcarboxamide-piperazine

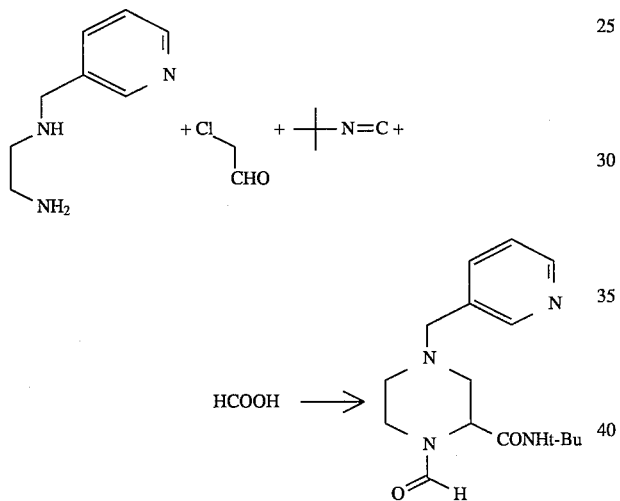

| 3-Picolyl ethylenediamine | 15.0 g (0.1 mol) |
| Chloroacetaldehyde 50 wt % in H₂O | 12.3 mL (0.1 mol) |
| Sodium formate | 6.76 g (0.1 mol) |
| tert-Butyl isocyanide | 9.07 g (0.11 mol) |
| 1-Propanol | 105 mL |

To a solution of 3-picolyl ethylenediamine in 1-propanol was added the sodium formate, the chloroacetaldehyde solution and the tert-butyl isocyanide. The reaction mixture was stirred for 20 h at 25° C. and then quenched by the addition of brine (75 mL) and 45% KOH (5 mL). The organic phase was removed and washed again with brine (75 mL). After the addition of 100 mL of isopropyl acetate, the solution was dried over Na₂SO₄ and treated with Darco G 60 activated charcoal. The filtered solution was evaporated to an oil. Chromatography on SiO2 (EtOAc/MeOH 90/10 to EtOAc/MeOH 50/50) gave 1-carboxy-4-(3-picolyl)-2-tert-butylcarboxamide-piperazine as a white solid. mp 127° C. ¹³C NMR (CDCl₃) 167.5, 162.0, 150.4, 149.2, 136.6, 132.2, 123.4, 59.9, 58.0, 52.9, 52.1, 51.5, 43.7, 28.7 (The compound is a ca. 2:3 mixture of the two formamide rotamers, only shifts of the major rotamer were reported.).

EXAMPLE 3

4-(3-Picolyl)-2-tert-butylcarboxamide-piperazine

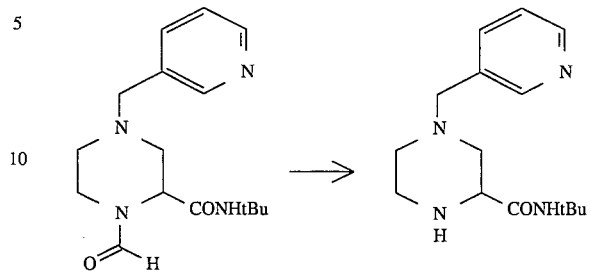

| 1-Carboxy-4-(3-picolyl)-2-tert-butylcarboxamide-piperazine | 1.23 g (4 mmol) |
| THF | 15 mL |
| HCl solution, 1N in water | 15 mL |

A solution of 1-carboxy-4-(3-picolyl)-2-tert-butylcarboxamide-piperazine in THF/H₂O/HCl was heated to 60° C. for 8 h. The solution was then evaporated to dryness to give 4-(3-picolyl)-2-tert-butylcarboxamide-piperazine as its hydrochloride salt. ¹³C NMR (D₂O) 163.5, 150.3, 143.9, 143.4, 130.6, 128.9, 57.3, 55.6, 53.1, 51.6, 48.7, 40.9, 28.3.

EXAMPLE 4

4-(3-Picolyl)-2-carbonitrile-piperazine

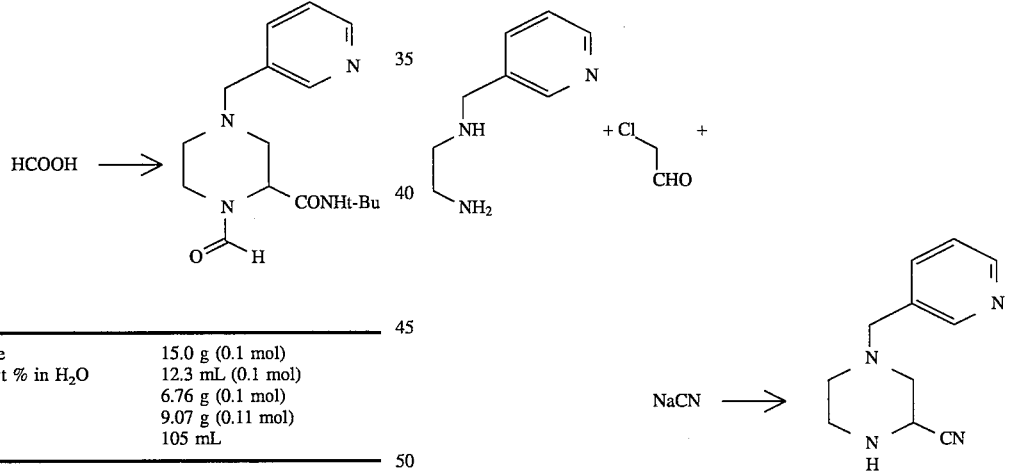

| 3-Picolyl ethylenediamine | 3.47 g (23 mmol) |
| Chloroacetaldehyde 50 wt. % in H₂O | 2.85 mL (23 mmol) |
| Sodium cyanide | 1.35 g (27.5 mmol) |
| Water | 57 mL |

To a solution of 3-picolyl ethylenediamine and sodium cyanide in water was added the aqueous chloroacetaldehyde solution. The reaction mixture was stirred at 25 ° C. for 20 h and solid NaCl was added to prepare a saturated solution. The NaCl saturated reaction mixture was then extracted with 400 mL of CHCl₃ and the organic phase was dried (MgSO₄), filtered and evaporated. Chromatography of the resulting oil on SiO₂ (EtOAC 100% to EtOAc/MeOH 80/20) and evaporation of the product containing fractions gave 4-(3-picolyl)-

2-carbonitrile-piperazine as a tan solid. mp 97° C.; $^{13}$C NMR (CDCl$_3$) 150.1, 149.0, 136.5, 132.9, 123.6, 118.9, 59.6, 54.6, 52.7, 46.3, 42.8.

EXAMPLE 5

4-(3- Picolyl)-2-tert-butylcarboxamide-piperazine

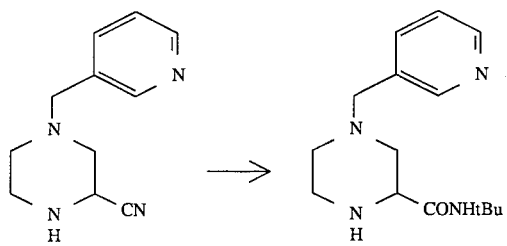

| 4-(3-Picolyl)-2-carbonitrile-piperazine | 0.283 g (1.4 mmol) |
|---|---|
| Glacial acetic acid | 3.5 mL |
| Sulfuric acid 96% | 1.6 mL |
| tert-Butanol | 2.5 mL |
| Water | 0.6 mL |

To a solution of 4-(3-picolyl)-2-carbonitrile-piperazine in HOAc was added 0.6 mL of H$_2$SO$_4$. The resulting precipitate was brought back into solution by the addition of 0.6 mL of H$_2$O and 1.5 mL of tert-butanol. TLC (EtOAc/MeOH 50/50) indicated only partial conversion after 24 h; thus, the remainder of the H$_2$SO$_4$ (1.0 mL) and tert-butanol (1.0 mL) were added. The reaction was complete after an additional 24 h. 45% Aqueous KOH solution was slowly added (to pH >12) and the mixture was extracted with 3×15 mL of CH$_2$Cl$_2$. The combined organic phases were dried over MgSO$_4$, filtered and concentrated to dryness to give a brown oil. Chromatography on SiO$_2$ (EtOAc/MeOH 50/50) gave 4-(3-picolyl)-2-tert-butylcarboxamide-piperazine as a low melting solid. $^{13}$C NMR (CD$_3$OD) 172.2, 150.9, 149.0, 139.2, 135.3, 125.2, 60.9, 59.7, 56.9, 53.8, 51.9, 44.8, 28.9.

EXAMPLE 6

4-Benzyl-2-carbonitrile-piperazine

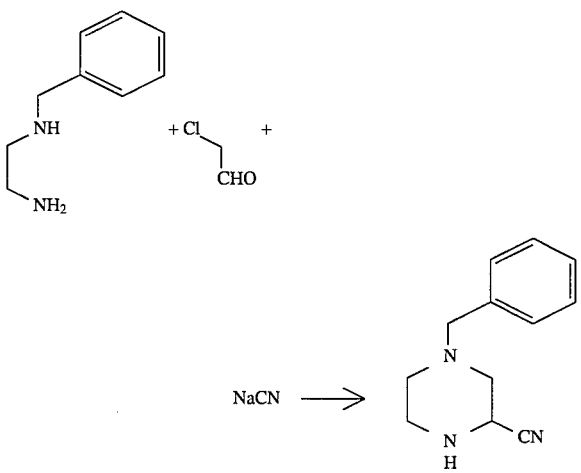

| N-Benzyl ethylenediamine | 0.79 g (5.26 mmol) |
|---|---|
| Chloroacetaldehyde 50 wt. % in H$_2$O | 0.65 mL (5.26 mmol) |
| Sodium cyanide | 0.310 g (6.31 mmol) |
| Sodium hydrogencarbonate | 0.98 g (10.5 mmol) |
| Water | 10 mL |

To a solution of N-benzyl ethylenediamine, sodium cyanide and sodium hydrogencarbonate in water was added the aqueous chloroacetaldehyde solution. The reaction mixture was stirred at 50° C. for 2 h. The reaction mixture was extracted with 40 mL of CH$_2$Cl$_2$ and the organic phase was dried (MgSO$_4$), filtered and evaporated. Chromatography of the resulting oil on SiO$_2$ (EtOAC 100%) and evaporation of the product containing fractions gave 4-benzyl-2-carbonitrile-piperazine as an oil; $^{13}$C NMR (CDCl$_3$) 137.5, 128.8, 128.4, 127.3, 119.6, 62.4, 54.5, 52.8, 46.5, 42.9.

EXAMPLE 7

(S)-4-(3-Picoly)-2-tert-butylcarboxamide-piperazine

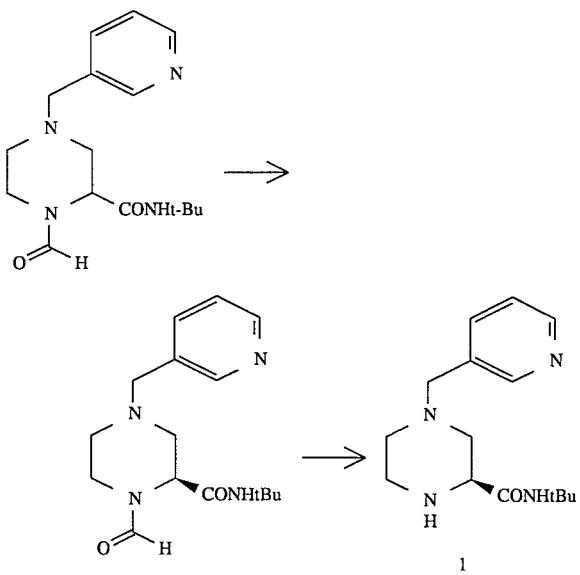

| Deprotection and Resolution of 1-Carboxy-4-(3-picolyl)-2-tert-butylcarboxamide-piperazine | |
|---|---|
| 1-Carboxy-4-(3-picolyl)-2-tert-butylcarboxamide-piperazine | 3.43 g (0.012 mol) |
| (1S)-(+)-10-Camphorsulfonic acid | 2.78 g (0.012 mol) |
| EtOH | 65 mL |
| EtOAc | 35 mL |

A mixture of 1-carboxy-4-(3-picolyl)-2-tert-butylcarboxamide-piperazine and (1S)-(+)-10-camphorsulfonic acid is heated to reflux in EtOH for 12 h. The reaction mixture is cooled to 0° C. and EtOAc is slowly added. A white precipitate forms and it is stirred for 12 h, filtered and dried to give 1-carboxy-4-(3-picolyl)-2-tert-butylcarboxamide-piperazine (+)-camphorsulfonic acid salt.

The camphorsulfonic acid salt is suspended in 20 mL of THF and is treated with 10 mL of 40% NaOH solution. The phases are seperated and the organic phase is washed with sat. aqueous K$_2$CO$_3$ solution. The organic phase is dried (K$_2$CO$_3$), filtered and the filtrate is evaporated to give (2S)-1-carboxy-4-(3-picolyl)-2-tert-butylcarboxamide-pip-

EXAMPLE 8

Conversion of Indene Oxide to
Cis-1-Amino-2-Indanol

| Materials | Mol. Wt. | Grams or ml | Millimoles |
|---|---|---|---|
| Indene oxide | 132 | 1 ml | 8.33 |
| Acetonitrile | 41 | 10 ml | 244 |
| Water | 18 | 2.15 ml | 119.4 |
| Conc. $H_2SO_4$ | 98 | 0.92 ml | 16.6 |
| 5N KOH | 57 | 3.0 ml | 15 |
| Dowex 50 × 4 (H+) | 1.9 meq/ml | 15 ml wet resin | 28.5 meq |
| Methanol | 17 | 50 ml | 50 |

To one ml of indene oxide (8.33 mmoles) dissolved in 10 ml acetonitrile was added 0.15 ml water (8.33 mmoles). The mixture was cooled to 0°–5° in an ice bath. Concentrated sulfuric acid was added dropwise while maintaining the batch temperature below 10°. When all the acid was added, the temperature was allowed to rise to 20°–25°. The clear solution was aged for 30 minutes.

To this mixture was added 2 ml of water and the solution heated for 30 minutes. When the methyl oxazoline was completely convened to cis amino indanol the reaction mixture was cooled to room temperature.

A solution of 5N KOH (3 ml, 15 mmoles) was added. This is 90% of theory for the sulfuric acid. The solution remained acid to litmus. If the pH rises above 2, re-acylation occurs and the yield of amino indanol is reduced. The white solid ($K_2SO_4$) was removed by filtration.

Dowex resin 15 ml (wet with acetonitrile) was added with stirring. The stirred resin was aged for 15 minutes and sampled for LC (dilx 50). When the LC peak for amino indanol disappeared, the resin was collected by filtration, washed with acetonitrile and then with methanol.

The wet resin was treated with a solution of 50 ml 1N $NH_3$ in methanol and the slurry stirred at room temperature for 30 minutes.

The resin was again collected by filtration and the methanol/$NH_3$ saved. Another charge of 1N $NH_3$/MeOH (20 ml) was added and the resin reslurried. After removal of the resin the methanol/$NH_3$ solutions of the amino indanol were combined and concentrated to remove the $NH_3$. Analysis of the final MeOH solution shows cis-1-amino-2-indanol ready for the tartaric acid resolving agent.

EXAMPLE 9

Preparation of racemic indene oxide

Indene (95%, 122 mL) was dissolved in methanol (812 mL) and acetonitrile (348 mL), then filtered. The filtrate was diluted with 0.05M sodium dibasic phosphate (116 mL), then adjusted to pH 10.5 with 1M aqueous sodium hydroxide. Aqueous hydrogen peroxide (35%, 105 mL) was diluted with water (53 mL) and added over 3 h, while maintaining the temperature at 25° C. and the internal pH at 10.5 with 1M aqueous sodium hydroxide (120 mL total).

After 6 h, 1M aqueous sodium metabisulfite was added (26 mL), while maintaining the pH above 8.3 by addition of 1M aqueous NaOH (39 mL). Water (700 mL) was added and the mixture extracted with methylene chloride (580 mL and 300 mL). The combined organic extracts containing indene oxide (117 g) were concentrated to a volume of 600 mL.

EXAMPLE 10

Preparation of (1S,2R)-indene oxide

The substrate, (1 S,2R)-indene oxide is prepared according to the method described by D. J. O'Donnell, et at., *J. Organic Chemistry*, 43, 4540 (1978), herein incorporated by reference for these purposes.

EXAMPLE 11

Preparation of cis-1-amino-2-indanol

Indene oxide (117 g) diluted to a total volume of 600 mL in methylene chloride was diluted with acetonitrile (600 mL) and cooled to −20° C. Methanesulfonic acid (114 mL) was then added. The mixture was warmed to 25° C. and aged for 2 h. Water (600 mL) was added and the mixture heated at 45° C. for 5 h. The organic phase was separated and the aqueous phase further heated at reflux for 4 h with concentration to approximately 200 g/L. The solution was adjusted to pH 12.5 with 50% aqueous sodium hydroxide, and then cooled to 5° C. and filtered, dried in vacuo, to provide cis 1-amino-2-indanol.

EXAMPLE 12

Preparation of 1S-amino-2R-indanol (1,S,2R)-indene oxide (85% ee,) (250 g, 0.185 mole) was dissolved in chlorobenzene (300 mL) and heptanes (1200 mL) and slowly added to a solution of methanesulfonic acid (250 mL, 0.375 mole) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2–3 h, then cooled to room temperature. Chlorobenzene (1000 mL) was added, the mixture stirred, and the organic phase separated. The remaining aqueous phase containing 1S-amino, 2R-indanol (85% ee, 165 g, 60%) was adjusted to pH 12 with 50% aqueous sodium hydroxide and the product collected by filtration and dried in vacuo at 40° C. to yield 1S-amino, 2R-indanol (85% ee).

EXAMPLE 13

Preparation of 1S-amino-2R-indanol (1S,2R)-indene oxide (85% ee,) (250 g, 0.185 mole) was dissolved in chlorobenzene (300 mL) and heptanes (1200 mL) and slowly added to a solution of fuming sulfuric acid (21% $SO_3$, 184 mL) in acetonitrile (1250 mL) at a temperature of less than about −10° C. The reaction mixture was warmed to 22° C. and aged for 1.0 h. Water was added to the mixture and concentrated by distillation until an internal temperature of 100° C. was achieved. The reaction mixture was heated at 100° C. for 2–3 h, then cooled to room temperature. Chlorobenzene (1000 mL) was added, the mixture stirred, and the organic phase separated. The remaining aqueous phase containing 1S-amino, 2R-indanol (85% ee) was diluted with an equal volume of acetonitrile. The pH was adjusted to 12.5 with 50% aqueous sodium hydroxide and the organic phase separated. The remaining aqueous phase was extracted with additional acetonitrile. The combined acetonitrile extracts were concentrated in vacuo to provide 1S-amino, 2R-indanol (85% ee).

Alternatively, the remaining aqueous phase containing 1S-amino-2R-indanol (85% ee) was diluted with an equal volume of butanol and the pH was adjusted to 12.5 with 50% aqueous sodium hydroxide and the organic phase separated. The organic phase was washed with chlorobenzene. L-tartaric acid was added and water was removed by distillation to crystallize the tartaric acid salt of the aminoindanol.

EXAMPLE 14

Use of benzonitrile

Indene oxide (5 g) was dissolved in benzonitrile (50 mL) at 25° C. and sulfuric acid (98%, 2.25 mL) was added. The mixture was diluted with 5M aqueous sodium hydroxide solution (50 mL) and extracted with methylene chloride. The organic extracts were concentrated in vacuo to give oxazoline.

EXAMPLE 15

Resolution of cis-1-Amino-2-indanol

Cis-1-Amino-2-indanol (100 g) was dissolved in methanol (1500 mL) and a solution of L-tartaric acid (110 g) in methanol (1500 mL) was added. The mixture was heated to 60° C. and cooled to 20° C., filtered and dried in vacuo to give 1S-amino, 2R-indanol L-tartaric acid salt as a methanol solvate.

EXAMPLE 16

Preparation of 1S-Amino-2R-indanol

1S-Amino, 2R-indanol L-tartaric acid salt methanol solvate (88 g) was dissolved in water (180 mL) and heated to 55°–60° C. The solution was clarified by filtration and the pH adjusted to 12.5 with 50% aqueous sodium hydroxide. The mixture was cooled to 0°–5° C. over 2 h, then aged at that temperature for 1 h, filtered, washed with cold water and dried in vacuo at 40° C. to yield 1S-amino, 2R-indanol (100% ee, 99% pure).

EXAMPLE 17

Conversion of 1,2 indanol to cis-1-amino-2-indanol

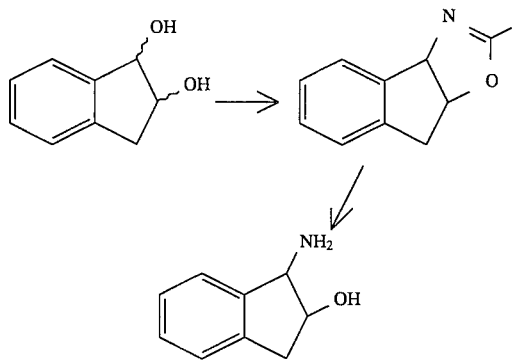

| Materials | Mol Wt | Grams or ml | Millimoles |
|---|---|---|---|
| 1,2 indane diol | 150 | 300 mg. | 2 |
| acetonitrile | 41 | 2.5 ml | 47.3 |
| water | 18 | 0.04 ml | 2 |
| sulfuric acid | 98 | 0.22 ml | 4 |
| 5 N KOH | 57 | 1.6 ml | 8.0 |
| Dowex 50 × 4 (H+) | | 10 ml | |
| methanol (1 m NH3) | | 30 ml | |

To 300 mg indane diol dissolved in 3 ml of acetonitrile containing 0.04 ml water was added dropwise at 0°–10° C. a volume of 0.22 ml of concentrated $H_2SO_4$. After the addition was complete, the ice bath was removed and the batch warmed to room temperature. After a 30 minute age, the clear solution was sampled for LC assay (dilx 500). When all the glycol was consumed, the solution was treated further with water and heated to reflux on a steam bath to hydrolyze the oxazoline.

When Ic analysis showed hydrolysis complete, 1.6 ml 5N KOH was added to neutralize the sulfuric acid. Potassium sulfate was s filtered from the solution.

The filtrate was assayed for cis amino indanol and contained 196 mg (66% of theory, which is also 75% corrected for unreacted starting material). The solution was passed over 10 ml of Dowex 50×4 (H+). The column spents were checked for product. All the amino indanol was adsorbed. After washing the resin with methanol, the product was eluted with a solution 1M in $NH_3$ (dry). The ammoniacal methanol was concentrated to remove the $NH_3$ and the final solution of amino-indanol ready for resolution was assayed. (175 mg, or 59% of theory when uncorrected for unreacted glycol).

EXAMPLE 18

Preparation of Indanol Reactants

Compounds (±)-trans-2-bromo-1-indanol were prepared by methods of S. M. Sutter et al., *J. Am. Chem. Soc.*, 62, 3473 (1940); and D. R. Dalton et at., *J. C. S. Chem. Commun.*, 591 (1966). Compounds (+)-trans-2-bromo-1-indanol and cis- and trans-1,2-indandiols were prepared by the methods of M. Imuta et at., *J. Org. Chem.*, 43, 4540 (1978).

EXAMPLE 19

Preparation of cis-1-amino-2-indanol from trans-2-bromo-1-indanol

Trans-2-bromo-1-indanol (10 g, 46.9 mmole diluted in 100 mL of acetonitrile containing 0.8 mL water) was cooled to –5° C. and concentrated sulfuric acid (5.2 mL) was added. The mixture was aged for 1 h, then 5M aqueous potassium hydroxide was added to adjust the pH to 11. The reaction mixture was filtered, removing the potassium sulfate salts. The aqueous acetonitrile filtrate was adjusted to pH less than 2 with sulfuric acid and heated to 80°–100° C., removing acetonitrile by distillation to provide an aqueous solution of cis-1-amino-indanol. The solution was concentrated to a volume of 20 mL, then adjusted to pH 12.5 with potassium hydroxide. The product crystallizes, was filtered and dried in vacuo to provide cis-1-amino-2-indanol.

EXAMPLE 20

Preparation of cis-1S-amino-2R-indanol from cis-(1S,2R)-indandiol

Cis-(1S,2R)-indandiol (1 g) was dissolved in acetonitrile (10 mL), cooled to 0° C. and concentrated sulfuric acid (1.0 mL) was added. The mixture was aged for 40 minutes with warming to 20° C. Water (0.8 mL) was added and the mixture was heated to reflux. Aqueous 5M potassium hydroxide (1.6 mL) was added to adjust the pH s to more than 11 and the resulting solid (potassium sulfate) removed by filtration to provide an aqueous solution of the cis-1S-amino-2R-indanol.

EXAMPLE 21

Preparation of cis-1-amino-2-indanol from trans-1,2-indandiol

Cis-1,2-indandiol (1.5 g) was dissolved in acetonitrile (25 mL) cooled to 0° C, and concentrated sulfuric acid (1.1 mL) was added. The mixture was gradually warmed to 20° C. and aged to 3 hours. Water (2 mL) was added and the mixture heated to reflux. Concentrated aqueous sodium hydroxide was added to adjust the pH to 12. The resulting solid was removed by filtration to provide an aqueous acetonitrile solution of cis-1-amino-2-indanol.

EXAMPLE 22

Preparation of cis-1-amino-2-indanol from cis-1,2-indandiol

Cis-1,2-indandiol (1.0 g) was dissolved in acetonitrile (20 mL), cooled to −40° C., and fuming sulfuric acid (21% $SO_3$, 0.8 mL) was added. The mixture was aged for 1 hour with gradual warming to 0° C. Water was added and the mixture heated to 80° C. for 1 hour to provide an aqueous solution of cis-1-amino-2-indanol.

EXAMPLE 23

Preparation of Amide 14

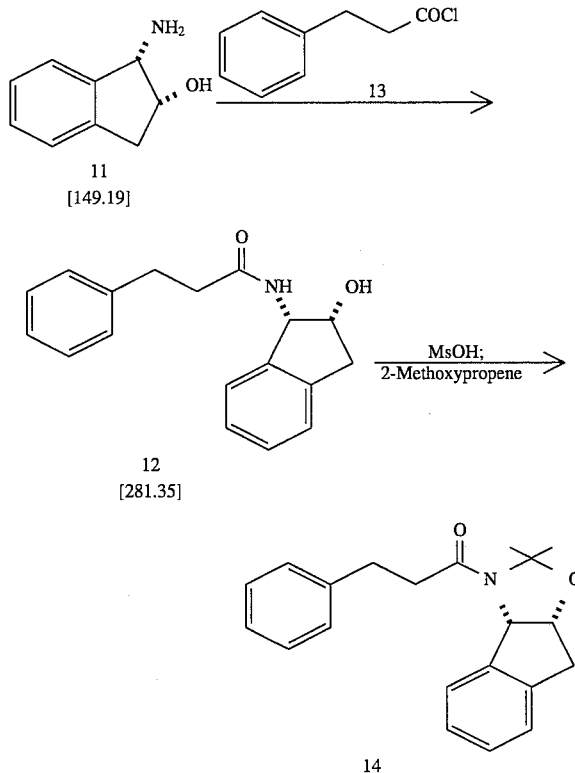

| | | |
|---|---|---|
| (−)-cis-1-aminoindan-2-ol (11) (99.7 wgt. %, 99.9 area %, >99.5% ee) | 900 g | 6.02 mol |
| sodium carbonate monohydrate | 760 g | 6.13 mol |
| diethoxymethane (DEM) | 56.3 L | |
| 3-phenylpropionyl chloride (13) | 1.05 kg | 6.23 mol |
| methanesulfonic acid (MSA) | 18.6 g | 0.19 mol |
| 2-methoxypropene (95% by GC) | 1.28 L | 13.3 mol |
| 5% aqueous $NaHCO_3$ | 10.8 L | |
| water | 26.2 L | |

A slurry mixture consisting of (−)-cis-1-aminoindan-2-ol (11, 900 g, 6.02 mol) in 40 L of DEM and aqueous sodium carbonate solution (760 g, 6.13 mol, of $Na_2CO_3 \cdot H_2O$ in 6.4 L of water) in a 100 L reactor with four inlets, equipped with a thermocouple probe, mechanical stirrer, and a nitrogen inlet adapter and bubbler, was heated to 46°–47° C. and aged for 15 minutes. The reaction mixture was heated to 46°–47° C. and aged for 15 minutes to insure dissolution of the solids. The aqueous phase had a pH of 11.5. Neat 3-phenylpropionyl chloride 13 (1.05 kg, 6.23 mol) was added over 2 h between 47° C. to 59° C. The internal temperature increased from 47° C. to 59° C. during the addition of 13; the hydroxyamide 12 crystallized out of solution during the acid chloride addition. After the addition was complete, the reaction mixture was aged at 59° C. for 0.5 h and then warmed to 72° C. to insure dissolution of the solids. The temperature was increased to 72° C. to dissolve the hydroxyamide so that a homogeneous sample can be obtained for HPLC assay and to simplify the phase cuts. Progress of the reaction was monitored by HPLC analysis: 60:40 Acetonitrile/5.0 mM of each $KH_2PO_4$ and $K_2HPO_4$. Approximate retention times:

| retention time (min.) | identity |
|---|---|
| 4.1 | hydroxy amide 12 |
| 6.3 | cis-aminoindanol 11 |
| 12.5 | ester amide by product |

After complete acid chloride addition and 0.5 h age at 72° C., the HPLC assay of the reaction mixture showed ~0.6 area % of 11, ~0.2 area % of ester amide by product and 98.7 area % of hydroxyamide. The hydroxy amide 12 was not efficiently rejected in the isolation of acetonide 14. The aqueous phase was separated and the organic phase was washed twice with 4.5 L of water. The washed organic phase was concentrated and dried via atmospheric azeotropic distillation. The initial volume of ~40 L was concentrated to 27 L. A total of 16 L of fresh DEM was charged to the still and the batch was concentrated at 88° C. to 89° C. to 40 L.

The dried DEM slurry of hydroxyamide 12 was treated with 1.28 L of 2-methoxypropene followed by 18.6 g of MSA at 30° C. The addition of MSA in absence of 2-methoxypropene resulted in the formation of an amine ester. This impurity reconverts to hydroxyamide 12 during the basic work up at the end of the acetonide formation. The pH of 1.0 mL sample diluted with 1.0 mL water was found to be 2.8–3.0. The resulting mixture was aged at 39° C. to 40° C. for 3 h. The acetonide formation was monitored by HPLC analysis using the same conditions as described above in this example. Approximate retention times:

| retention time (min.) | identity |
|---|---|
| 4.1 | hydroxy amide 12 |
| 6.9 | methylene ketal impurity |
| 9.0 | acetonide 14 |
| 12.5 | ester amide by product |

The mixture was aged at 38°–40° C. until 12 is <0.4 A %. A typical HPLC area % profile is as follows: 0.4 area % of hydroxyamide 12, 96.9 area % of acetonide 14, 0.2 area % of ester amide by product, 1.1 area % of methylene ketal impurity. The reaction mixture was cooled to 24° C. and quenched with 10.8 L of 5% aqueous sodium bicarbonate solution. The aqueous phase was separated and the organic phase was washed twice with 10.8 L of water. The pH of the water wash was 7.6. If the pH was too low, the acetonide group could be hydrolyzed back to give the hydroxyamide 12. The washed organic phase (34.2 L) was concentrated via atmospheric distillation at 78° C. to 80° C. to final volume of 3.5 L. The acetonide concentration was made ~525 g/L to minimize isolation losses. The hot DEM solution of 14 was allowed to cool to 57° C., seeded with 0.5 g of 14 and further cooled to 0° C. and aged for 0.5 h. The batch started to crystallize out of solution between 53° C. to 55° C. The product was isolated by filtration and the wet cake was washed with cold (0° C.) DEM (300 mL). The washed cake was dried under vacuum (26" of Hg) at 30° C. to afford acetonide 14 (90%, >99.5 area % by HPLC).

EXAMPLE 24

Preparation of Acetonide 14 from (11•tartaric acid) salt

| | | |
|---|---|---|
| (–)-cis-1-aminoindan-2-ol tartrate salt methanol solvate (44.3 wt. % of free base 11) | 100 g | 297 mmol |
| sodium carbonate monohydrate | 63.76 g | 514 mmol |
| diethoxymethane (DEM) | 2.83 L | |
| 3-phenylpropionyl chloride (13) | 52.7 g | 312 mol |
| methanesulfonic acid (MSA) | 0.95 g | 9.86 mmol |
| 2-methoxypropene (95% by GC) | 63 mL | 658 mmol |
| 5% aqueous NaHCO₃ | 520 mL | |
| water | 1.32 L | |

A slurry mixture consisting of (–) 11•tartrate salt methanol solvate (100 g, 44.3 g of free base, 297 mmol) in 2.0 L of (DEM) and aqueous sodium carbonate solution (63.8 g, 514 mmol, of $Na_2CO_3 \cdot H_2O$ in 316 mL of water) in a 5.0 L reactor with four inlets, equipped with a thermocouple probe, mechanical stirrer, and a nitrogen inlet adapter and bubbler, was heated to 50° C. Heating the reaction mixture to 60° C. did not dissolve all the solids. Neat 3-phenylpropionyl chloride 13 (52.7 g, 312 mmol) was added over 30 min at 50° C. and the mixture was aged at 50° C. for 15 min. Progress of the reaction was monitored by HPLC analysis: 60:40 Acetonitrile/5.0 mM of each $KH_2PO_4$ and $K_2HPO_4$, 1.0 mL/min. Approximate retention times:

| retention time (min.) | identity |
|---|---|
| 4.1 | hydroxy amide 12 |
| 6.3 | cis-aminoindanol 11 |
| 12.5 | ester amide by product |

After complete acid chloride addition and 15 min. age at 50° C., the HPLC assay of the slurry mixture showed ~0.1 area % of 11. After this point, the reaction mixture was heated to 75° C.

The temperature was increased to 75° C to dissolve the hydroxyamide 12 in DEM and simplify the phase separations. The aqueous phase was separated and the organic phase was washed twice with water (250 mL). The sodium tartrate was removed in the aqueous phase. The first aqueous cut had a pH of 8.98. The pH of the two water washes were 9.1 and 8.1, respectively. The washed organic phase was concentrated and dried via atmospheric distillation. Approximately 1.0 L of distillate was collected and 750 mL of fresh DEM was charged back to the distillation pot. The atmospheric distillation was continued until another 350 mL of distillate was collected. The solution KF was 93 mg/L.

The dried DEM solution was cooled to 30° C. and treated with 63 mL of 2-methoxypropene followed by 0.95 g of MSA. The pH of 1.0 mL sample diluted with 1.0 mL water is 3.2. The reaction mixture was aged at 35°–42° C. for 2 h. The acetonide formation was monitored by HPLC analysis using the same conditions as described above in this Example. Approximate retention times: same as above. The mixture is aged at 38°–40° C. until 12 is <0.7 A %. A typical HPLC area % profile is as follows: 0.4 area % of hydroxy amide, 96.9 area % of acetonide 14, 0.2 area % of ester amide by product, 1.1 area % of methylene ketal impurity. The reaction mixture was cooled to 20° C., filtered to remove the cloudy appearance and quenched with 520 mL of 5% aqueous sodium bicarbonate solution. The aqueous phase was separated and the organic phase was washed with 500 mL of water. The pH of the water wash is 7.4. The washed organic phase (~2.0 L) was concentrated via atmospheric distillation at 78° C. to 80° C. to final volume of 1.0 L. The acetonide concentration in the isolation was maintained at ~525 g/L to minimize isolation losses. The hot DEM solution of 14 was allowed to cool to 50°–52° C., seeded with 100 mg of product and further cooled to 5° C. and aged for 20 min. The batch started to crystallize out of solution at 50° C. The product was isolated by filtration and the wet cake was washed with cold (0° C.) DEM (2×40 mL). The washed cake was dried under vacuum (26" of Hg) at 30° C. to afford acetonide 14 (87.9%, >99.5 area % by HPLC).

EXAMPLE 25

Preparation of Acetonide 14 (Isopropyl Acetate Solvent)

| | | |
|---|---|---|
| (–)-cis-1-aminoindan-2-ol (11) (98.5 wgt. %) | 80 g | 535 mmol |
| isopropyl acetate (IPAC) | 1.2 L | |
| water | 560 mL | |
| 5N sodium hydroxide | 116 mL | 580 mmol |
| 3-phenylpropionyl chloride (13) | 90.8 g | 539 mmol |
| methanesulfonic acid (MSA) | 1.1 mL | 17.0 mmol |
| 2-methoxypropene (95% by GC) | 119 mL | 1.24 mol |
| 5% aqueous NaHCO₃ | 950 mL | |
| water | 400 mL | |
| methyl cyclohexane | 2.25 L | |

A mixture of of (–)-cis-1-aminoindan-2-ol 11 (80 g, 535 mmol) in 1.2 L of IPAC and 560 mL of water was treated with 5 (90.8 g, 539 mmol) while the pH maintained between 8.0–10.5 at 70°–72° C. with 5N sodium hydroxide (116 mL, 580 mmol).

Progress of the reaction was monitored by HPLC analysis: 60:40 Acetonitrile/5.0 mM of each $KH_2PO_4$ and $K_2HPO_4$.
Approximate retention times:

| retention time (min.) | identity |
|---|---|
| 4.1 | hydroxy amide 12 |
| 6.3 | cis-aminoindanol 11 |
| 12.5 | ester amide by product |

At the end of the reaction, the aqueous phase was separated and the organic phase was washed with water (400 mL) at 72° C.–73° C. The pH of the aqueous phase and the aqueous wash was 8.1 and 7.9, respectively. The wet IPAC phase was dried via atmospheric distillation. A total of 3.0 L of IPAc was charged to lower the batch KF to <100 mg/L. The final volume is ~1.60 L. The resulting IPAC slurry of hydroxyamide 12 was treated with 2-methoxypropene (119 mL, 1.24 mol) followed by MSA (1.1 mL, 3.2 mole %) at 35° C.–38° C. for 4.5 h. The acetonide formation was monitored by HPLC analysis using the same conditions as described above. The mixture was aged at 38°–40° C. until 12 is <0.4 area %. The reaction was filtered to remove the hazy precipitate and the filtrate was quenched into cold sodium bicarbonate solution (950 mL) over 15 min. The aqueous phase was separated and the organic phase was washed with water (400 mL). The sodium bicarbonate solution was cooled to 0° C.–5° C. The pH of the aqueous phase and the aqueous wash was found to be 7.5 and 7.9, respectively. Atmospheric distillation was carded out while the solvent was switched to methylcyclohexane from IPAC. The initial volume before atmospheric concentration was 1.65 L. A total of 1.5 L of methylcyclohexane was added to complete the solvent switch to methylcyclohexane from IPAC. The batch temperature at the end of the solvent switch was 101° C. and the final batch volume was ~900 mL. The batch was heated to 65° C.–70° C. to insure dissolution of the solids, then cooled to 55° C., seeded with the product and cooled to 0° C. The mixture was aged at 0° C. for 15 min and the product was isolated by filtration and washed with cold methylcyclohexane (200 ml). The washed cake was dried under vacuum (26" of Hg) at 30° C. to afford acetonide 14 (87.5%, >99.5 area % by HPLC).

EXAMPLE 26

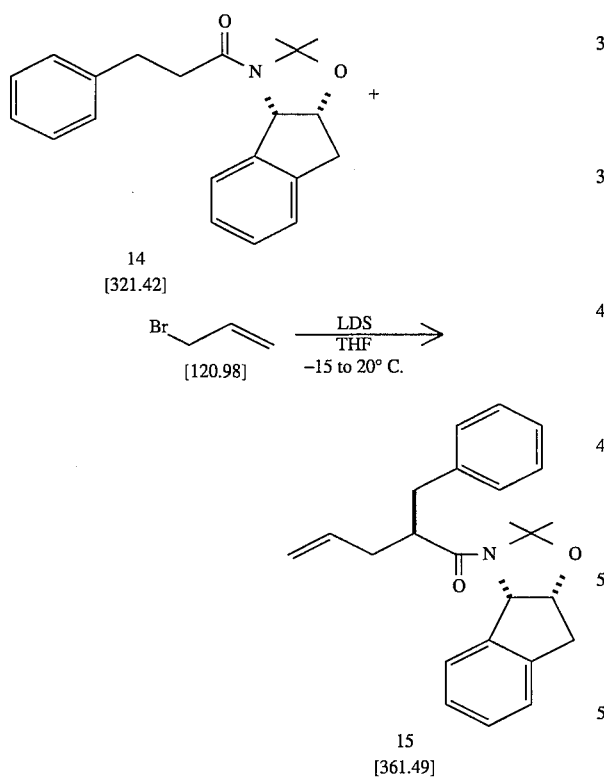

| Acetonide (14) (99.1 wt. %) | [321.42] | 200 g | | 0.617 mol |
| --- | --- | --- | --- | --- |
| Allyl Bromide | [120.98] | 77.6 g | 53.6 mL | 0.642 mol |
| LDS (FMC 9404) | 1.32 M in THF | | 518 mL | 0.684 mol |
| Citric acid | [192.1] | 35.73 g | | 0.186 mol |
| THF sieve dried | | | 1.43 L | |
| Water | | | 1.05 L | |
| 0.3 M H₂SO₄ | | | 1.18 L | |
| 6% NaHCO₃ IPAc | | | 1.18 L | |

The crystalline acetonide 14 (200 g, 0.622 mol, 99.1 wt. %). was dissolved in 1.25 L sieve dried THF (KF=11 mg/L) under nitrogen atmosphere at 25° C. with mechanical stirring. The resulting KF of the solution at this point was 40 mg/L. The solution was subjected to three alternating vacuum/nitrogen purge cycles to thoroughly degas the solution of dissolved oxygen.

Allyl bromide was added to the THF solution. The resulting KF was 75 mg/L. Typical complete conversion (>99.5%) has been obtained with pre-LDS solution KF levels of 200 mg/L with the 10% base excess present in this procedure. The solution was then cooled to −20° C. A THF solution of lithium hexamethyldisilazide (LDS, 1.32M) was added to the allyl bromide/14 solution at such a rate as to maintain the reaction temperature at −20° C. The LDS addition took 30 min. The mixture was aged at −15° to −20° C. and quenched when the conversion was >99%. Analysis of the reaction was carried out by HPLC. Approximate retention times: hydroxyacetonide by product =5.3 min, ethyl benzene=5.6 min, acetonide 14=6.6 min; allyl acetonide 15=11.8 min; epi-15=13.3 min. After 1 h, the reaction had gone to >99.5% conversion. The reaction was quenched by the addition of a solution of citric acid (35.7 g, 0.186 mol) in 186 mL of THF. The mixture was aged at 15° C. for 30 min following the citric acid addition. The mixture was concentrated at reduced pressure (about 28" Hg) to about 30% of the initial volume while maintaining a pot temperature of 11°–15° C. and collecting 900 mL of distillate in a dry ice-cooled trap. The solvent was then switched using a total of 2.7 L of isopropyl acetate (IPAc) while continuing the reduced pressure distillation. The solvent switch was stopped when <1 mole % THF remained by ¹H NMR (see analytical report for GC method). The maximum temperature during the distillation should not exceed 35° C. The crude mixture in IPAc was washed with 1.05 L of distilled water, 1.18 L of 0.3M sulfuric acid, and 1.18 L of 6% aqueous sodium bicarbonate. The volume of the organic phase after the washes was 1.86 L.

The pH of the mixture after the three aqueous washes was 6.5, 1.3 and 8.5, respectively. HPLC analysis of the mixture at this point indicated 93–94% assay yield for 15. The ratio of the desired 15:epi-15 was 96:4 by HPLC (same conditions as above). GC analysis at this point indicated that the hexamethyldisilazane by-product had been completely removed in the workup.

EXAMPLE 27

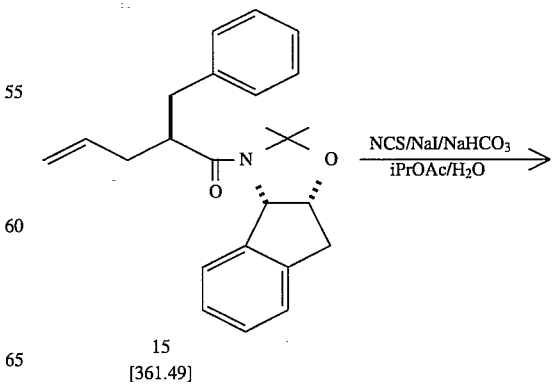

-continued

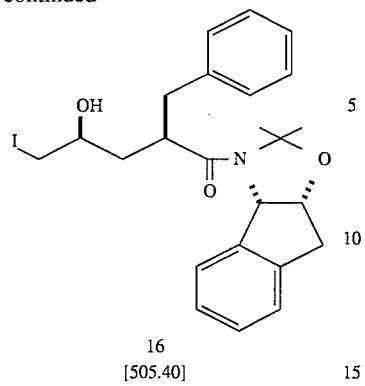

16
[505.40]

| NCS | [133.5] | 141.2 g | 1.06 mol |
| NaHCO₃ | [84.01] | 36.6 g | 0.434 mol |
| NaI | [149.9] | 158.6 g | 1.06 mol |
| Na₂SO₃ | [126.0] | 80 g | |
| Water | 1.55 L | | |

To the allyl amide 15 solution in IPAc from the previous step at 25° C. was added a solution of 36.6 g of sodium bicarbonate in 1.03 L of distilled water and the biphasic mixture was cooled to 5° C. Solid N-chlorosuccinimide (141.2 g, 1.06 mol) was added. There was no exotherm after the addition of NCS. To this mixture was added an aqueous solution of sodium iodide (158.6 g, 1.06 mol) while maintaining the reaction mixture at 6°–11° C. The addition took 30 min, and the mixture became dark. The mixture was warmed to 25° C. and aged with vigorous stirring. Progress of the reaction was monitored by HPLC: same system as above, approximate retention times: iodohydrins 16, epi-16, bis-epi-16=8.1 min; allyl amide 15=11.8 min. Analysis of the mixture by HPLC after 2.25 h indicated >99.5% conversion. The approximate diastereomer ratio of 16:epi-16:bis-epi-16 in the crude mixture is roughly 94:2:4 at this point when resolution of the components can be obtained on this system. The agitation was discontinued and the layers were separated. To the organic phase was added aqueous sodium sulfite (80 g, 0.635 mol in 400 mL) over 10–15 min. The temperature of the mixture rose from 26°–29° C. after the sodium sulfite addition. The mixture was agitated for 40 min at 25° C. The solution was substantially decolorized after the sulfite wash. The layers were separated; the KF of the organic phase at this point was 25 g/L. The volume of the organic phase was 1.97 L. Quantitative analysis of the mixture by HPLC (same system as above) indicated a 86% overall assay yield of the iodohydrin 16 at this point (corrected for coeluting diastereomers).

EXAMPLE 28

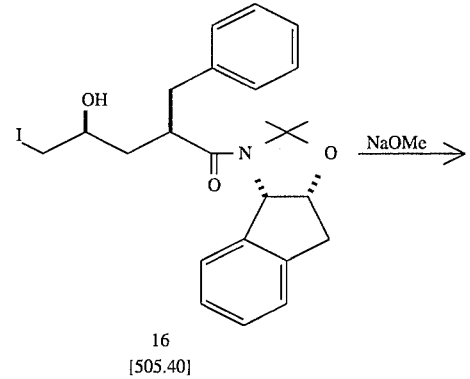

16
[505.40]

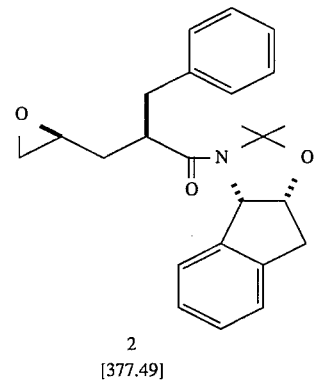

2
[377.49]

| NaOMe [54.02] | d = 0.945 | 25 wt % in MeOH | 172 g |
| 0.796 mol | | | |
| 3% aqueous Na₂SO₄ | | | 1.5 L |
| n-PrOH | | | |

The solution of the iodohydrin 16 was concentrated in vacuo (28" Hg) to azeotropically dry the batch. A total of 700 mL of distillate was collected while maintaining a batch temperature of 22°–28° C. The distillate was replaced with 500 mL of IPAc (KF=275 mg/L).

The solution was cooled to 26° C. and 25% NaOMe/MeOH solution (168.1 g) was added over a 10 min period. The temperature dropped to 24° C. after the addition of sodium methoxide. The mixture became darker and a gummy solid briefly formed which redissolved. The mixture was aged for 1 h at 25° C. Analysis of the reaction was carded out by HPLC (same conditions as above), approximate retention times: epoxide epi-2=6.5 min, epoxide 2, bis-epi-2=7.1 min, iodohydrin 16=8.1 min. HPLC analysis indicated 99% conversion of the iodohydrin to the epoxide. After an additional 40 min, 4.1 g of the sodium methoxide/methanol solution was added. After 20 min, HPLC analysis indicated 99.5% conversion. The reaction was quenched by the addition of 366 mL of water at 25° C. which was then agitated briefly (10 min) and the layers were separated. It was subsequently found that extended aging of the reaction and water wash agitation/settling gave substantial back reaction to iodohydrin under these conditions in the pilot plant. This problem is especially acute in the water washes. To eliminate this problem, the reaction was run at 15° C. After >99% conversion was achieved (1 h after NaOMe addition), the mixture was diluted with IPAc (40% of batch volume) and initially washed with an increased volume of water (732 mL) at 20° C. Colder temperatures and more concentrated mixtures can result in the premature precipitation of 2 during the washes. The agitation/settling times were kept to a minimum (10 min/30 min, respectively). In this way, the back reaction could be limited to ≦1%. Crude mixtures containing (97:3) epoxide 2/iodohydrin 16 have been carried forward in the isolation to afford epoxide product containing 0.6% iodohydrin. Epoxide product containing this level of iodohydrin has been carried forward without complication. The organic phase was washed with 3% aqueous sodium sulfate (2×750 mL). The volume of the organic phase was 1.98 L after the washes. The pH of the three water washes was 10.7, 9.4 and 8.6, respectively. HPLC analysis indicated a 86% overall assay yield of epoxide 2 at this point (corrected for 4% co-eluting bis-epi-2). The IPAc solution of epoxide 2 was concentrated at reduced pressure (28" Hg) to a volume of about 600 mL while maintaining the batch at 15°–22° C. The solvent was switched to n-PrOH by adding 750 mL n-PrOH while vacuum concentrating to a pot volume of about 500 mL, maintaining the batch at <30° C. Temperatures >35° C. during the concentration/solvent switch can give an n-propyl ether by-product derived from epoxide 2. Analysis of the solvent composition by $^1$H NMR showed <1 mol % IPAc remaining. The thick slurry was cooled to −10° C. over an hour and aged for 45 min. The solids were filtered and washed with 125 mL of cold nPrOH. The product was dried in a vacuum oven at 25° C. to afford epoxide 2 (98.9 A %, 97.6 wt. %, 0.8 wt. % epi-2) Normal phase HPLC indicated no bis-epi-2 present in the isolated solids.

EXAMPLE 29

N-[2(R)-hydroxy-1(S)-indanyl]-5-[(2(S)-tertiary-butylaminocarbonyl)-4-(3-pyridylmethyl)piperazino]-4(S)-hydroxy-2(R)-phenylmethylpentanamide monohydrate (J•H$_2$O)

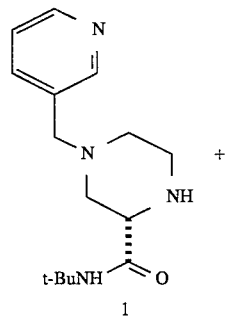

1

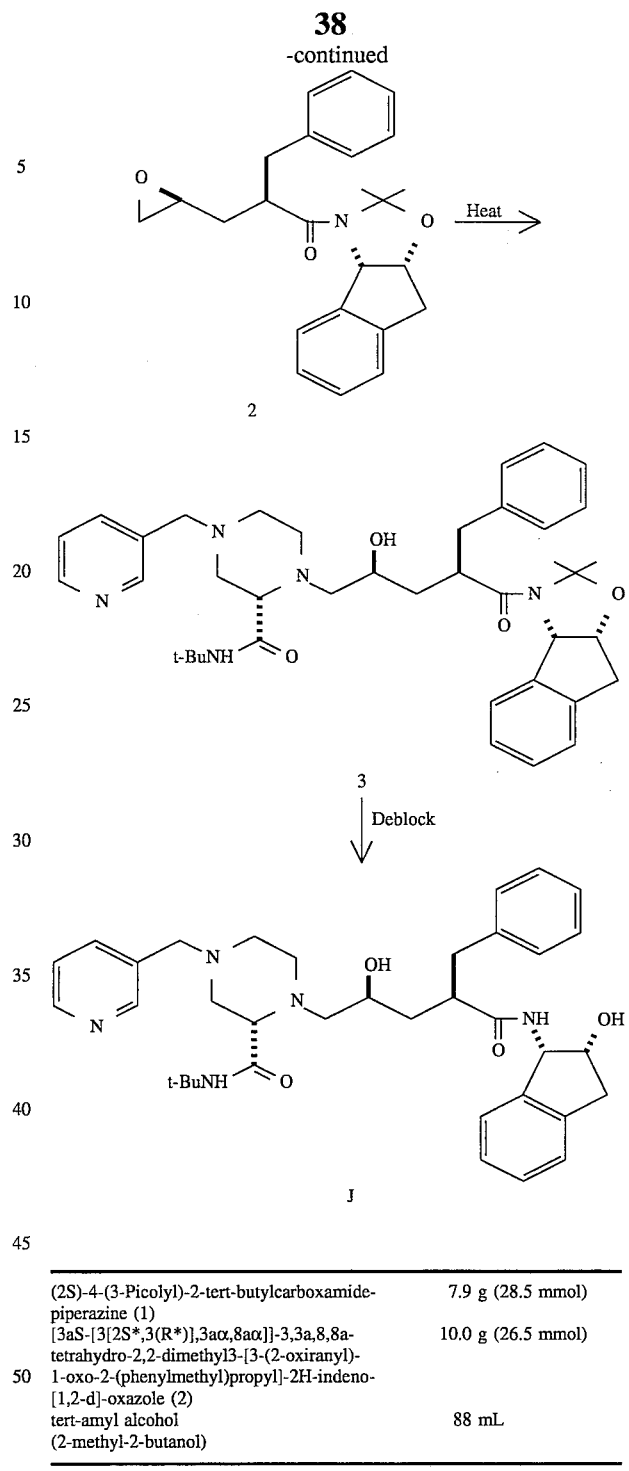

| (2S)-4-(3-Picolyl)-2-tert-butylcarboxamide-piperazine (1) | 7.9 g (28.5 mmol) |
|---|---|
| [3aS-[3[2S*,3(R*)],3aα,8aα]]-3,3a,8,8a-tetrahydro-2,2-dimethyl3-[3-(2-oxiranyl)-1-oxo-2-(phenylmethyl)propyl]-2H-indeno-[1,2-d]-oxazole (2) | 10.0 g (26.5 mmol) |
| tert-amyl alcohol (2-methyl-2-butanol) | 88 mL |

A mixture of 1 (7.9 g, 28.5 mmol) and the epoxide 2 (10 g, 26.5 mmol) in isopropyl alcohol (88 mL) was heated to the reflux point 82° C. and held for 72 h to complete the formation of 3.

The solution of 3 is cooled to 0° C. and treated with anhydrous HCl gas and the mixture is aged between 0°–5° C. for 3 h. The hydrolysis was quenched by the slow addition of 50% NaOH to adjust the pH of the mixture to 12 while keeping the temperature less than 25° C.

The mixture is then partitioned with isopropyl acetate (200 mL) and water (50 mL). The mixture was agitated and the layers were separated and the aqueous phase was reextracted with isopropyl acetate (50 mL).

The isopropyl acetate solution of J is concentrated to about 100 g/L and water is added to saturate the hot isopropyl acetate solution. The mixture was seeded and cooled to afford Compound J from epoxide 2.

While the foregoing specification teaches the principles of the present invention, with examples provided for the purpose of illustration, it will be understood that the practice of the invention encompasses all of the usual variations, adaptations or modifications, as come within the scope of the following claims and it equivalents.

What is claimed is:

1. A process for forming a compound (F)

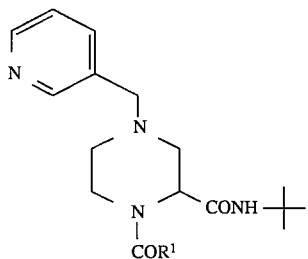

wherein $R^1$ is selected from hydrogen, $C_{1-10}$ alkoxy, mono-, di-, or tri-halogenated $C_{1-10}$ alkyl or aryl;

comprising reacting an imine (C)

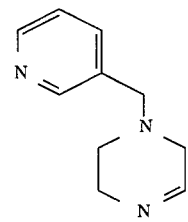

with t-butyl-NC in the presence of a carboxylic acid, $R^1$—$CO_2H$, to form the compound (F)

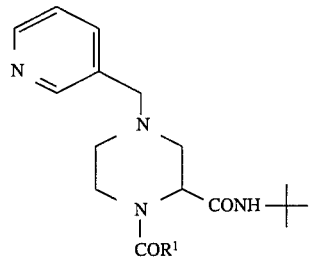

* * * * *